(12) United States Patent
Cushman et al.

(10) Patent No.: US 6,509,344 B1
(45) Date of Patent: Jan. 21, 2003

(54) INDENOISOQUINOLINES AS ANTINEOPLASTIC AGENTS

(75) Inventors: Mark S. Cushman, West Lafayette, IN (US); Pamela M. Nagafuji, Arlington, MA (US); Muthusamy Jayaraman, Woburn, MA (US); Yves G. Pommier, Bethesda, MD (US)

(73) Assignees: The United States of America as represented by the Department of Health and Human Services, Washington, DC (US); Office of Technology Transfer National Institute of Health, Rockville, MD (US)

( * ) Notice: Subject to any disclaimer, the term of this patent is extended or adjusted under 35 U.S.C. 154(b) by 0 days.

(21) Appl. No.: 09/807,340

(22) PCT Filed: Oct. 14, 1999

(86) PCT No.: PCT/US99/23900

§ 371 (c)(1),
(2), (4) Date: Jul. 20, 2001

(87) PCT Pub. No.: WO00/21537

PCT Pub. Date: Apr. 20, 2000

Related U.S. Application Data

(60) Provisional application No. 60/104,226, filed on Oct. 14, 1998.

(51) Int. Cl.[7] .................. A61K 31/473; A61K 31/4741; C07D 221/18; A61P 35/00
(52) U.S. Cl. .................. 514/280; 514/284; 546/48; 546/61
(58) Field of Search ................................ 514/280, 284; 546/48, 61

(56) References Cited

U.S. PATENT DOCUMENTS 5,597,831 A    1/1997   Michalsky et al.

OTHER PUBLICATIONS

Wawzonek S. (1982) Organic Preparations and Procedures Int. 14(3), 163–168.*
Sof'ina et al. (1980) Experimental Evaluation of Antitumor Drugs in the USA and USSR and Clinical Correlations. NIH Publication No. 80–1933.*
Cushman et al., "Stereoselective Oxidation by Thionyl Chloride Leading to the Indeo[1,2–c]isoquinoline System," *J Org Chem, 43*(19):3781–3783 (1978).
Cushman et al., "Synthesis and Biological Activity of Structural Analogues of the Anticancer Benzophenanthridine Alkaloid Nitidine Chloride," *J Med Chem, 27*(4):544–547 (Apr. 1984).
Cushman et al., "Synthesis and Antitumor Activity of Structural Analogues of the Anticancer Benzophenanathridine Alkaloid Fagaronine Chloride," *J Med Chem, 28*(8):1031–1306 (Aug. 1985).
Jayaraman et al., "Novel Oxidative Transformation of Indenoisoquinolines to Isoquinoline–3–spiro–3'–phthalides in the Presence of Osmium Textraoxide and 4–methylmorpholine N–oxide," *J Org Chem, 63*(17): 572–573 (Aug. 1998).
Perez–Chiesa et al., "Evaluation of Genotoxicity of the Indenoisoquinoline Analogues of Fagaronine and Nitidine in Drosophila melanogaster," *Mutation Research, 301*(4):207–212 (Apr. 1993).
Wawzonek et al., "The Synthesis and Reactions of 1–Carbamyl–11–ketoindeno[1,2–c]isoquinoline," *J Org Chem, 31*:1004–10064 (Apr. 1966).
Wawzonek, "Synthesis of 6–substituted–6–H–indeno[1,2–c]isoquinoline–5–11–diones," *Chemical Abstracts, 96*(23):653–654, Abstract No. 199485x (Jun. 1982).

* cited by examiner

*Primary Examiner*—Evelyn Mei Huang
(74) *Attorney, Agent, or Firm*—Leydig, Voit, & Mayer, Ltd.

(57) ABSTRACT

A number of indenoisoquinolines were prepared and evaluated for cytotoxicity in human cancer cell cultures and for activity versus topoisomerase I. The two most cytotoxic indenoisoquinolines proved to be cis-6-ethyl-5,6,12,13-tetrahydro-2,3-dimethoxy-8,9(methylenedioxy)-5,11-dioxo-11H-indeno[1,2-c]isoquinoline and cis-6-allyl-5,6,12,13-tetrahydro-2,3-dimethoxy-8,9-(methylenedioxy)-5,11-dioxo-(11H)indeno[1,2-c]isoquinoline. Two of the most potent topoisomerase I inhibitors were 6-(3-carboxy-1-propyl)-5,6-dihydro-5,11-dioxo-11H-indeno[1,2-c]isoquinoline (26) and 6-ethyl-2,3-dimethoxy-8,9-(methylenedioxy)-11H-indeno[1,2-c]isoquinolinium chloride (27). Two additional potent topoisomerase I inhibitors, 6-allyl-5,6-dihydro-2,3-dimethoxy-8,9-(methylenedioxy)-5,11-dioxo-11H-indeno[1,2-c]isoquinoline (13c) and 5,6-dihydro-6-(4-hydoxybut-1-yl)-2,3-dimethoxy-8,9-methylenedioxy-5,11 dioxo-(11H)-indeno[1,2-c]isoquinoline (19a), did not unwind DNA and did not affect topoisomerase II.

54 Claims, 1 Drawing Sheet

INDENOISOQUINOLINES AS ANTINEOPLASTIC AGENTS

This application is the 371 of PCT/US99/23900, filed on Oct. 14, 1999, which claims the priority of provisional application No. 60/104,226, filed on Oct. 14, 1998.

GOVERNMENT RIGHTS

This invention was made with Government support under Grant No. NO1-CM-67260 awarded by the National Institutes of Health. The government has certain rights in the invention.

FIELD OF THE INVENTION

The present invention relates to compositions and a method for treating a patient having cancer. More specifically, the present invention is directed to novel indenoisoquinoline derivatives and to their use in cancer therapy.

BACKGROUND AND SUMMARY OF THE INVENTION

The control and cure of cancer represents one of our most challenging health problems. The treatment of cancer can be approached by several modes of therapy including surgery radiation, chemotherapy or a combination of any of these treatments. Chemotherapy continues to be an indispensable therapy for inoperable or metastatic forms of the disease. Thus, the discovery of compounds specifically targeting cancer cells, or the cellular mechanisms involved in the proliferation of cancer cells, can provide significant advancement in the eradication or control of cancer.

The selection of compounds having effective anticancer activity is complicated by the still limited knowledge of cancer cell biology and biochemistry. Therefore, development of new effective anti-cancer agents remains heavily dependent on screening of new compounds for cytotoxic activity. Antineoplastic drug candidates exhibit enhanced cytotoxicity against cancer cells relative to normal cells. Methods of screening for anticancer activity have focused on several targets: (1) the ability of a compound to inhibit tumor growth and/or progression in animal studies; (2) inhibition of cell growth/proliferation in cell lines of cancerous origin; and (3) inhibition of intracellular processes necessary for the growth or propagation of cancer cells.

The mouse L1210 leukemia cell line was initially the preferred model system used for screening compounds for anti-cancer activity. However, the P388 murine leukemia system was found to be more sensitive and predictive than L1210

The mouse L1210 leukemia cell line was initially the preferred model system used for screening compounds for anti-cancer activity. However, the P388 murine leukemia system was found to be more sensitive and predictive than L1210 leukemia system; it has been used as a primary screen during the past decade. Systematic screening for compounds exhibiting toxicity to these two cell lines has resulted in the isolation of a large number of active natural products. However, the anticancer activities of these compounds were predominantly for leukemia, lymphoma and a few rare tumors. Low clinical efficacy, or the lack of clinical efficacy of known chemotherapeutics against slower growing solid tumors, is aserious concern.

Considering the diversity of cancer in terms of cell type, morphology, growth rate and other cellular characteristics, the U.S. National Cancer Institute (NCI) has developed a "disease-oriented" approach to anticancer activity screening (M. R. Boyd, in "Principle of Practice of Oncology" J. T. Devita, S. Hellman, S. A. Rosenberg (Eds.) Vol. 3, PPO Update, No. 10, 1989). This in vitro prescreening system is based on the measurement of anticancer cytotoxicity against human cancer cell line panels consisting of approximately 60 cell lines of major human cancers (including leukemia and slower growing tumor cells such as lung, colon, breast, skin, kidney, etc.) and is referred hereinafter as "COMPARE" screening. An important advantage of the new in vitro screening panels is the opportunity to facilitate identification of compounds that are selectively more cytotoxic to cells of certain types of cancers, thus increasing the ability to select compounds for further study with respect to specific diseases.

The compounds of the present invention were screened for antineoplastic activity using the COMPARE screening methodology. The results demonstrate that the compounds are antineoplastic agents for use in treating human cancers.

Anticancer agents are known to act through a variety of mechanisms to destroy or inhibit the proliferation of cancer cells. For example, some agents are antimetabolites which act as false substrates in the biochemical processes of cancer cells. One compound which has this mechanism of action is methotrexate, an analog of folic acid, which functions in part by binding to dihydrofolate reductase, thereby preventing the formation of guanine and adenine from the folic acid precursor molecule. Thus, methotrexate inhibits the ability of cancer cells to construct DNA by inhibiting the proper metabolism of folic acid.

Other anticancer agents act by alkylating DNA strands, thereby producing defects in the normal double helical structure of the DNA molecule. This alkylation may cause the formation of breaks and inappropriate links between (or within) strands of DNA. Such disruption of the DNA structure, if not repaired by intracellular repair mechanisms, impairs the cell's ability to replicate it's DNA. Examples of alkylating anticancer agents are cyclophosphamide and chlorambucil.

Some anticancer agents target the intracellular mechanisms involved in replication of the DNA strand itself. Replication of a cell's genetic material requires a means to pull the DNA double helix apart into two strands. This separation is typically accomplished by the enzyme topoisomerase I. Disruption of the function of this enzyme results in DNA strand breaks in cells that are dividing, thereby causing the death of the dividing cell. Because cancer cells grow and reproduce at a much faster rate than normal cells, they are more vulnerable to topoisomerase inhibition than are normal cells. Thus, agents that inhibit topoisomerase I are known to be potent anticancer agents. The drug camptothecin was shown to be an inhibitor of topoisomerase I and a potent anticancer agent; unfortunately, camptothecin also produced toxic side effects. The search for potent inhibitors of topoisomerase I with lessened toxicity to normal cells continues.

Many of the compounds of the present invention caused inhibition of topoisomerase I, to varying extents. Therefore, it appears that some of the growth inhibition demonstrated through COMPARE testing occurs through this mechanism of action. However, several of the indenoisoquinolines of the present invention were surprisingly potent cell growth inhibitors even though their inhibitory effects on topoisomerase I were relatively small in comparison to other agents tested. These data demonstrate that the novel indenoisoquinolines of the present invention cause inhibition of cell growth, at least in part, through another mechanism of action besides inhibition of topoisomerase I. The present invention describes novel indenoisoquinoline compounds, many of which are potent inhibitors of topoisomerase I, and are useful as anticancer agents. Further, the present invention describes novel indenoisoquinoline compounds which are potent inhibitors of cell growth, and are thus potent anticancer agents.

DETAILED DESCRIPTION OF THE INVENTION

Figure 1:
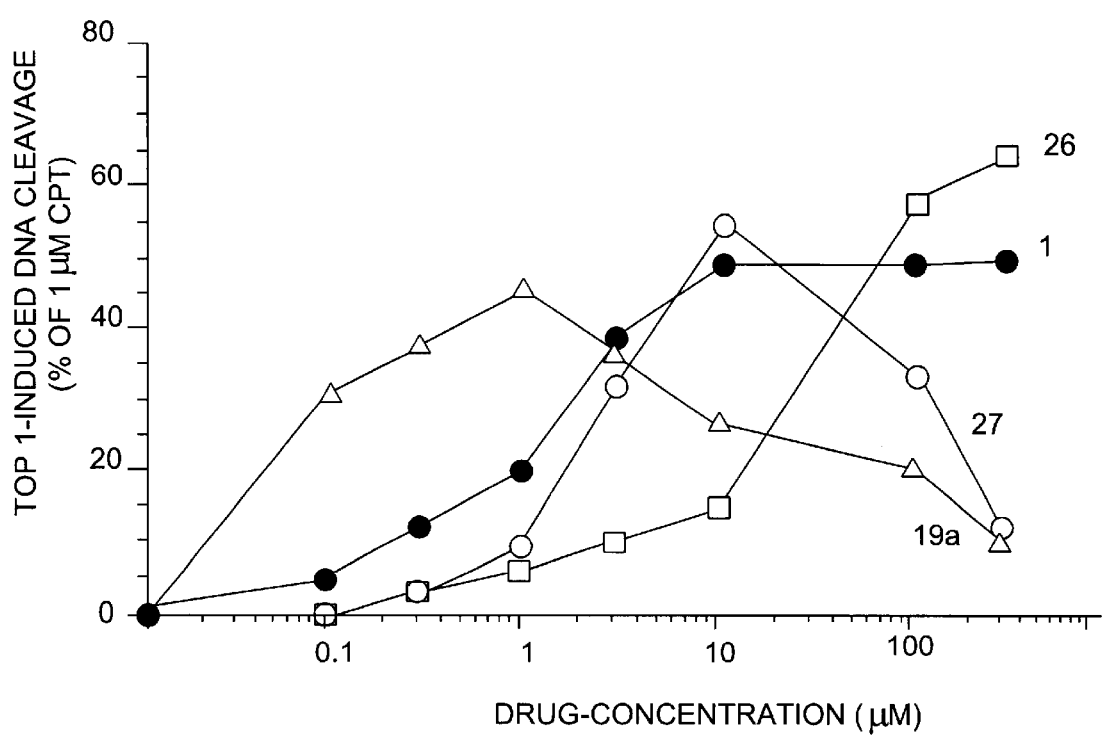
FIG. 1 is a line graph depicting topoisomerase I (TOP-I)-induced DNA cleavage (% of 1 $\mu$M camptothecin (CPT)) versus the drug concentration $\mu$M of four compounds: 1, 19a, 26 and 27.

The compounds of this invention are represented by the general formula:

(Formula I)

wherein the group designated $R_1$ is hydrogen, formyl, phenyl, phenyl substituted with $C_1$–$C_6$ alkoxy or $C_1$–$C_6$ alkyl, or $R_1$ is a group —(CH$_2$)$_m$Z, wherein m is 1–6 and Z is selected from the group consisting of hydrogen, hydroxy, carboxy, formyl, $C_1$–$C_6$ alkyl, carbo-($C_1$–$C_6$ alkoxy), $C_2$–$C_6$ alkenyl, phenyl, $C_1$–$C_6$ alkylamino, and $C_1$–$C_6$ hydroxyalkylamino;

- $R_2$, $R_2'$ and $R_4$ are independently selected from the group consisting of hydrogen, $C_1$–$C_6$ alkyl, $C_2$–$C_6$ alkenyl, $C_1$–$C_6$ alkoxy, phenoxy and benzyloxy, or $R_2$ and $R_2'$ taken together form a group of the formula —OCH$_2$O—;
- $R_3$ and $R_3'$ are independently selected from the group consisting of hydrogen, $C_1$–$C_6$ alkyl, $C_1$–$C_6$ alkoxy, $C_2$–$C_6$ alkenyl, phenoxy, and benzyloxy, or $R_3$ and $R_3'$ taken together form a group of the formula —OCH$_2$O—;
- wherein n=1 or 0, and bond a is a single bond when n=1, and bond a is a double bond when n=0;
- provided that when $R_2$, $R_2'$, $R_4$, $R_3$ and $R_3'$ are hydrogen, Z is not $C_1$–$C_6$ hydroxyalkylamino; and
- further provided that when $R_1$ is methyl, $R_3$ and $R_3'$ are independently selected from the group consisting of hydrogen, $C_1$–$C_6$ alkyl, $C_1$–$C_6$ alkoxy, $C_2$–$C_6$ alkenyl, phenoxy, and benzyloxy.

In one preferred embodiment of the compounds of this invention of Formula I, the protons on the carbon atoms at fusion bond a are in a cis-configuration across bond a.

In one embodiment of the present invention, the compound of Formula I has the following substituents: $R_1$ is —(CH$_2$)$_m$ O4 and m is 3–6; n is zero (0) and a is a double bond; and $R_2$, $R_2'$, $R_3$, $R_3'$ and $R_4$ are hydrogen.

In another embodiment of the present invention, the compound of Formula I has the following substituents: $R_1$ is $C_2$–$C_4$ alkyl or $C_2$–$C_4$ alkenyl; $R_2$ and $R_2'$ are $C_1$–$C_4$ alkoxy; $R_3$ and $R_3'$ taken together form a group of the formula —OCH$_2$O—; and $R_4$ is hydrogen.

Another embodiment of the present invention includes the compound of Formula I wherein: $R_1$ is (CH$_2$)$_m$OH and m is 3–6; n is zero (0) and a is a double bond; $R_2$ and $R_2'$ are $C_1$–$C_3$ alkoxy; $R_3$ and $R_3'$ taken together form a group of the formula —OCH$_2$O—; and $R_4$ is hydrogen.

A further embodiment of the present invention includes the compound of Formula I wherein: $R_1$ is $C_1$–$C_3$ alkyl or $C_2$–$C_4$ alkenyl; n is one (1) and a is a single bond; $R_3$ and $R_3'$ taken together form a group of the formula —OCH$_2$O—; and $R_4$ is hydrogen.

Another embodiment of the present invention includes the compound of Formula I wherein: $R_1$ is —(CH$_2$)$_m$COOH and m is 1–4; n is zero (0) and a is a double bond; and $R_2$, $R_2'$, $R_3$, $R_3'$ and $R_4$ are hydrogen.

Other compounds of the present invention are represented by the following formula:

(Formula II)

wherein
- $R_1$ is phenyl or phenyl substituted with $C_1$–$C_6$ alkoxy or $C_1$–$C_6$ alkyl, or $R_1$ is a group —(CH$_2$)$_m$Z wherein m is 1–6 and Z is selected from the group consisting of hydrogen, hydroxy, carboxy, formyl, $C_1$–$C_6$ alkyl, carbo-($C_1$–$C_6$ alkoxy), $C_2$–$C_6$ alkenyl, phenyl, $C_1$–$C_6$ alkylamino, and $C_1$–$C_6$ hydroxyalkylamino, provided that when Z is hydrogen, m is 2–6;
- $R_2$, $R_2'$ and $R_4$ are independently selected from the group consisting of hydrogen, $C_1$–$C_6$ alkyl, $C_2$–$C_6$ alkenyl, $C_1$–$C_6$ alkoxy, phenoxy and benzyloxy, or $R_2$ and $R_2'$ taken together form a group of the formula —OCH$_2$O—;
- $R_3$ and $R_3'$ are independently selected from the group consisting of hydrogen, $C_1$–$C_6$ alkyl, $C_1$–$C_6$ alkoxy, $C_2$–$C_6$ alkenyl, phenoxy, and benzyloxy, or $R_3$ and $R_3'$ taken together form a group of the formula —OCH$_2$O—; and
- wherein X is a pharmaceutically acceptable anion.

A "pharmaceutically acceptable anion" is defined as any non-toxic mono-, di-, or trivalent anions. Exemplary of such are Br$^-$, Cl$^-$, SO$_4^{-2}$, PO$_4^{-3}$, acetate, CO$_3^{-2}$ and HCO$_3^-$. It is understood that the stoichiometry of the salts of Formula II are dependent on the valence of the anion component and the ratio of cationic to anionic components is such as to provide a neutral salt.

In one embodiment of the present invention, a compound of Formula II has the following substituent groups: $R_1$ is $C_1$–$C_4$ alkyl; $R_2$ and $R_2'$ are $C_1$–$C_3$ alkoxy; $R_3$ and $R_3'$ taken together form a group of the formula —OCH$_2$—O—; and $R_4$ is hydrogen.

The present invention further provides pharmaceutical formulations comprising an effective amount of an indenoisoquinoline compound of this invention for treating a patient having cancer. As used herein, an effective amount of the indenoisoquinoline compound is defined as the amount of the compound which, upon administration to a patient, inhibits growth of cancer cells, kills malignant cells, reduces the volume or size of the tumors or eliminates the tumor entirely in the treated patient.

The effective amount to be administered to a patient is typically based on body surface area, patient weight, and/or patient condition. The interrelationship of dosages for animals and humans (based on milligrams per meter squared of body surface) is described by Freireich, E. J., et al., *Cancer Chemother. Rep.* 1966, 50 (4), 219. Body surface area may be approximately determined from patient height and weight (see e.g., Scientific Tables, Geigy Pharmaceuticals, Ardley, N.Y., pages 537–538 (1970)). An effective amount of the indenoisoquinoline compounds of the present invention is defined as any amount useful for inhibiting the growth of (or killing) cancer cells in a patient. Typically, such effective amounts range from about 5 mg/kg to about 500 mg/kg, more preferably from about 5 mg/kg to about 250 mg/kg, and most preferably about 5 to about 150 mg/kg. Effective doses will also vary, as recognized by those skilled in the art, dependent on route of administration, excipient usage and the possibility of co-usage with other therapeutic treatments including other anti-tumor agents, and radiation therapy.

The pharmaceutical formulation may be administered via the parenteral route, including subcutaneously, intraperitoneally, intramuscularly and intravenously. Examples of parenteral dosage forms include aqueous solutions of the active agent, in isotonic saline, 5% glucose or other well-known pharmaceutically acceptable liquid carrier. In one preferred aspect of the present embodiment, the indenoisoquinoline compound is dissolved in a saline solution containing 5% dimethyl sulfoxide and 10% Cremphor EL (Sigma Chemical Company). Additional solubilizing agents such as cyclodextrins, which can form specific, more soluble complexes with the present indenoisoquinoline compounds, or other solubilizing agents well-known to those familiar with the art, can be utilized as pharmaceutical excipients for delivery of the indenoisoquinoline compounds.

The present compound can also be formulated into dosage forms for other routes of administration utilizing well-known methods. The pharmaceutical compositions can be formulated, for example, in dosage forms for oral administration in a capsule, a gel soal or a tablet. Capsules may comprise any well-known pharmaceutically acceptable material such as gelatin or cellulose derivatives. Tablets may be formulated in accordance with conventional procedure by compressing mixtures of the active indenoisoquinoline and solid carriers, and lubricants well-known to those familiar with the art. Examples of solid carriers include starch, sugar and bentonite. The compounds of the present invention can also be administered in a form of a hard shell tablet or capsule containing, for example, lactose or mannitol as a binder and conventional fillers and tableting agents.

The examples provided illustrate various embodiments of Applicants' invention, and are not intended to in any way limit the scope of the invention as set forth in this specification and claims.

The synthesis of an indenoisoquinoline 1 has been previously reported. Compound 1 was subsequently found to be cytotoxic in human cancer cell cultures. More recently, a COMPARE analysis indicated that the cytotoxicity profile of 1 is similar to that of the topoisomerase I inhibitors camptothecin and saintopin. When tested for activity against topoisomerase, compound 1 was in fact found to induce DNA cleavage in the presence of topoisomerase I. However, the cleavage site specificity differed from that of camptothecin in that compound 1 did not cleave at all of the sites characteristic of camptothecin, while some DNA cleavage sites were unique to compound 1. In addition, compound 1 did not produce detectable DNA unwinding, suggesting that in contrast to other non-camptothecin topoisomerase inhibitors, it is not a DNA intercalator. The present invention describes the development of new topoisomerase I inhibitors and potential anticancer agents which have been developed based upon the activities associated with compound 1.

Chemistry

A number of indenoisoquinolines 3–8 lacking the methylenedioxy and methoxy substituents of 1 were synthesized by reacting commercially available benz[d]indeno[1,2-b]pyran-5,11-dione (2) with various primary amines (Scheme1). The reactions were carried out at room temperature in chloroform and the yields were generally high.

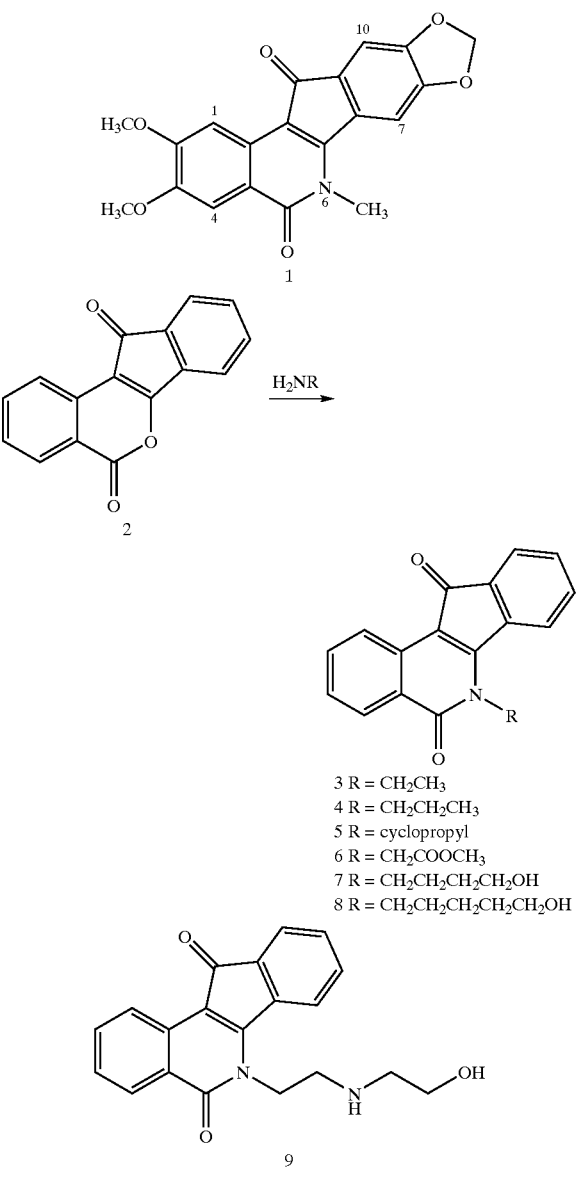

In order to accommodate additional substituents on the two aromatic rings of the indenoisoquinoline system, an alternative synthesis was executed which was based on the condensation of Schiff bases 11 with homophthalic anhydrides 10 to afford cis substituted isoquinolones 12, followed by conversion to the desired products 13 in the presence of thionyl chloride (Scheme 2). Using this method, a series of eleven additional indenoisoquinolines 13a–13k were synthesized. These compounds incorporate a variety of substituents at C-2, C-3, N-6, C-8, C-9, and C-10 of the ring system.

A modification of this route was carried out in order to synthesize compounds containing an alcohol group at the end of an alkyl chain located at N-6 (Scheme 3). Treatment of 4-amino-1-butanol (14a) or 5-amino-1-pentanol (14b) with tert-butyldimethylsilyl chloride according to the procedure of Corey and Venkateswarlu (*J. Am. Chenz. Soc.* 1972, 94, 6190–6191) afforded the corresponding protected intermediates 15a and 15b. The imines 17a and 17b were synthesized by treating the O-TBDMS protected aminols 15a and 15b with piperonal (16) in chloroform in the presence of anhydrous magnesium sulfate. Condensation of the Schiff bases 17a and 17b with 4,5-dimethoxyhomophthalic anhydride (10b) afforded the cis 3,4-disubstituted isoquinolones 18a and 18b. The cis stereochemistry of 18a and 18b was confirmed by 6 Hz coupling constant observed for the C-3 and C-4 methine signals. Treatment of 18a or 18b with thionyl chloride resulted in deprotection of the terminal alcohol, allowing a Friedel-Crafts reaction to form the five-membered ring, and dehydrogenation to afford 19a and 19b.

Several dihydro derivatives 20–23 were also prepared (Scheme 4). The syntheses of 20 and 23 were carried out as described previously. Compounds 21 and 22 were prepared by treatment of the acids 12k and 12c with Eaton's reagent (10% $P_2O_5$, in methanesulfonic acid). Treatment of 21 with borane-tetrahydrofuran complex in refluxing THF for 1 hour resulted in reduction of the ketone to afford 24. When 21 was treated with the same reagent in refluxing THF for 12 hours, reduction of both the ketone and amide carbonyls occurred to yield 25. The stereochemistry of the hydroxyl group results from the approach of the reducing reagent to the less sterically hindered, convex surface of the indenoisoquinoline 21.

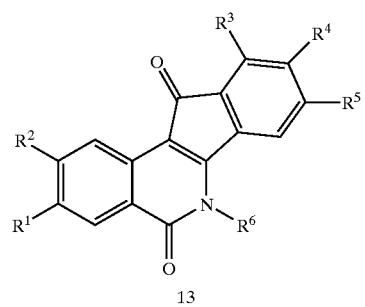

13

| | $R^1$ | $R^2$ | $R^3$ | $R^4$ | $R^5$ | $R^6$ |
|---|---|---|---|---|---|---|
| a | H | H | H | O—$CH_2$—O | | $CH_3$ |
| b | H | H | H | O—$CH_2$—O | | $CH_2CH_2CH_2CH_3$ |
| c | $OCH_3$ | $OCH_3$ | H | O—$CH_2$—O | | $CH_2CH=CH_2$ |
| d | $OCH_3$ | $OCH_3$ | H | O—$CH_2$—O | | $CH_2CH_2CH_2CH_3$ |
| e | $OCH_3$ | $OCH_3$ | H | O—$CH_2$—O | | $CH_2Ph$ |
| f | $OCH_3$ | $OCH_3$ | H | O—$CH_2$—O | | $C_6H_5$-p-$OCH_3$ |
| g | H | H | H | OBn | OBn | $CH_3$ |
| h | $OCH_3$ | $OCH_3$ | H | OBn | OBn | $CH_3$ |
| i | $OCH_3$ | $OCH_3$ | $OCH_3$ | $OCH_3$ | $OCH_3$ | $CH_3$ |
| j | H | H | $OCH_3$ | $OCH_3$ | $OCH_3$ | $CH_3$ |
| k | $OCH_3$ | $OCH_3$ | H | O—$CH_2$—O | | $CH_2CH_3$ |

Scheme 3.

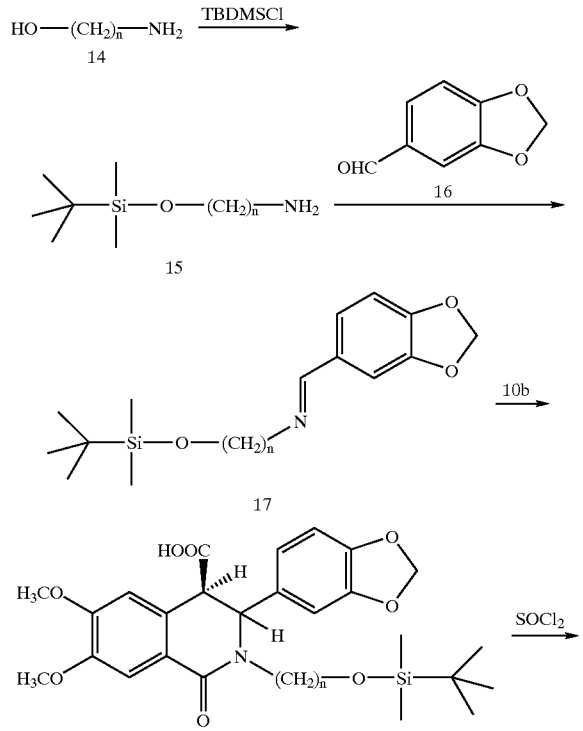

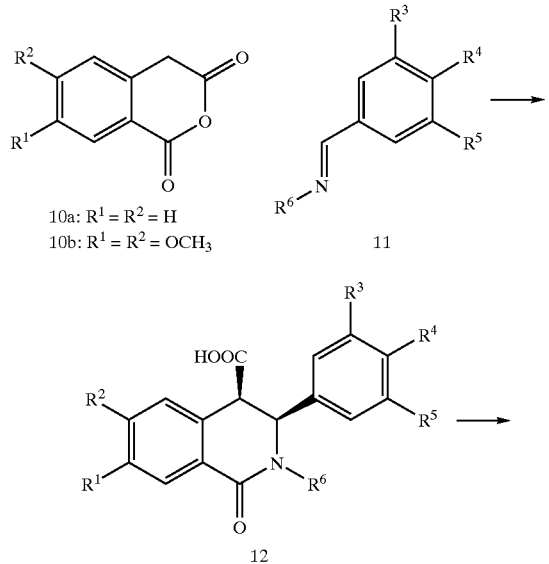

Scheme 2

-continued
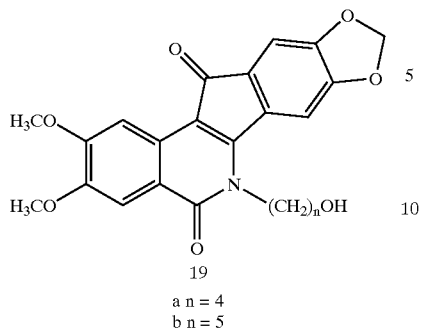
19
a n = 4
b n = 5
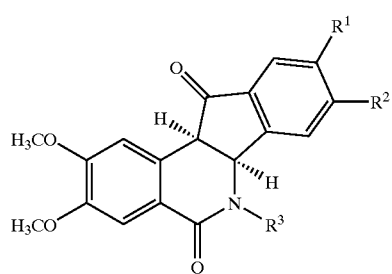
20 R¹, R² = OCH₂O; R³ = CH₃
21 R¹, R² = OCH₂O; R³ = CH₂CH₃
22 R¹, R² = OCH₂O; R³ = CH₂CH=CH₂
23 R¹ = OSO₂CH₃; R² = OCH₃; R³ = CH₃
24
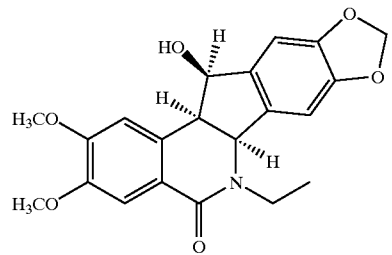
25
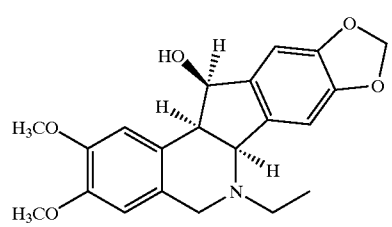
26
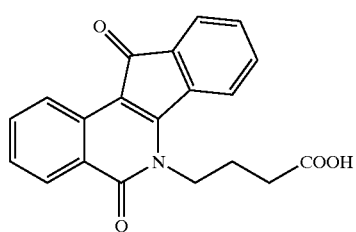
-continued
27
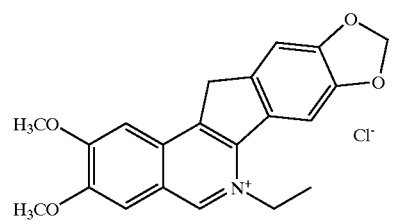
28
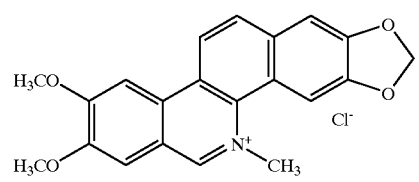
29
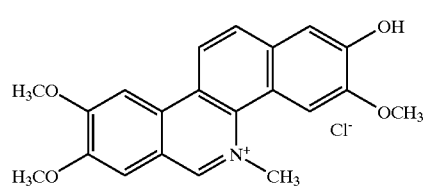
Scheme 5.
30
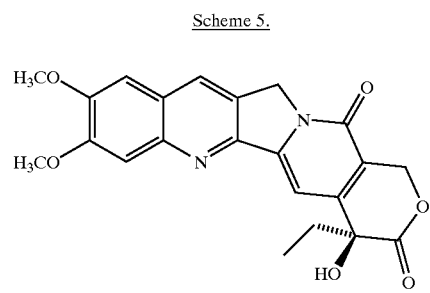
31
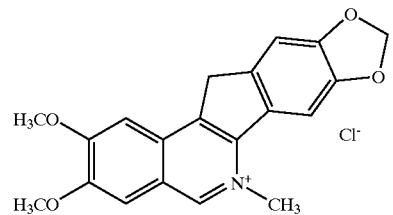
32
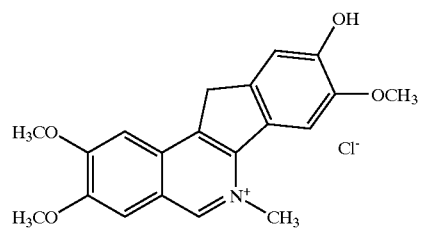

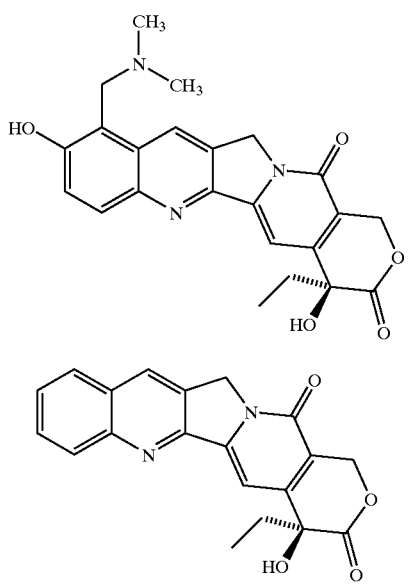

Dehydration, as well as dehydrogenation, of the alcohol 25 occurred in the presence of palladium in charcoal in refluxing acetic acid. Treatment of the product with aqueous NaCl provided the indenoisoquinolinium salt 27.

Finally, we were interested in obtaining an indenoisoquinoline derivative having an acidic group which might be converted into a more water-soluble salt. The carboxylic acid 26 was obtained by oxidation of indenoisoquinoline 7 with Jones reagent.

For comparison purposes, camptothecin (34) and several camptothecin derivatives 33 and 30, as well as nitidine (28), fagaronine (29), the anticancer indenoisoquinolinium species 31 and 32 (structures given in Scheme 5) were used as control agents for experiments examining topoisomerase I-mediated DNA cleavage and/or cell growth inhibition experiments.

Biological Results and Discussion

The indenoisoquinolines were examined for antiproliferative activity against the human cancer cell lines in the National Cancer Institute screen (COMPARE screening), in which the activity of each compound was evaluated with approximately 55 different cancer cell lines of diverse tumor origins. The GI50 values (i.e., the concentration causing 50% growth inhibition) obtained with selected cell lines, along with the mean graph midpoint (MGM) values, are summarized in Table 1. The MGM is based on a calculation of the average GI50 for all of the cell lines tested (approximately 55) in which GI50 values below and above the test range ($10^{-4}$ to $10^{-8}$ molar) are taken as the minimum ($10^{-8}$ molar) and maximum ($10^{-4}$ molar) drug concentrations used in the screening test. In addition, the relative activities of the compounds in the topoisomerase I cleavage assay are listed in Table 1. In Table 1, results of the topoisomerase I cleavage assay are listed as follows: 1) "++" designates those compounds having greater than 50% of the activity of 1 $\mu$M camptothecin; 2) "+" designates those compounds having between 20% and 50% of the activity of 1 $\mu$M camptothecin; 3) "±" designates those compounds having less than 20% of the activity of 1 $\mu$M camptothecin; and 4) "O" designates those compounds that were inactive in the topisomerase I cleavage assay.

TABLE 1

Cytotoxicities of Indenoisoquinoline Analogs
Cytotoxicity (GI50 in $\mu$M)[a]

| Compd. No. | Lung HOP-62 | Colon HCT-116 | CNS SF-539 | Melanoma UACC-62 | Ovarian OVCAR-3 | Renal SN12C | Prostate DU-145 | Breast MDA-MB-435 | MGM[b] | Top 1 Cleavage[c] |
|---|---|---|---|---|---|---|---|---|---|---|
| 1 | 1.3 | 35 | 41 | 4.2 | 73 | 68 | 37 | 96 | 20 | ++ |
| 2 | >100 | >100 | >100 | >100 | >100 | >100 | >100 | >100 | 85 | 0 |
| 3 | — | — | — | — | — | — | — | — | — | 0 |
| 4 | — | — | — | — | — | — | — | — | — | 0 |
| 5 | 61 | >100 | >100 | 84 | >100 | >100 | >100 | >100 | 98 | 0 |
| 6 | — | — | >100 | >100 | >100 | >100 | >100 | >100 | 81 | 0 |
| 7 | 13 | 3.2 | 4.6 | 4.4 | 74 | 7.4 | >100 | >100 | 16 | + |
| 8 | 4.4 | 3.9 | — | 14.3 | 93 | — | 3.4 | 41 | 14 | + |
| 13a | 22 | 54 | — | >100 | >100 | >100 | >100 | — | 45 | + |
| 13b | 17 | 2.9 | 9.0 | 8.2 | 94 | 37 | 38 | >100 | 30 | + |
| 13c | 3.4 | 2.3 | 2.2 | — | 6.6 | 2.6 | 3.2 | 5.2 | 4.2 | + |
| 13d | 16 | 45 | — | 21 | 78 | — | 16 | >100 | 42 | + |
| 13e | 12 | >100 | — | 50 | >100 | — | 4.0 | >100 | 42 | ± |
| 13f | 20 | >100 | >100 | >100 | >100 | >100 | 76 | >100 | 70 | 0 |
| 13g | 72 | >100 | >100 | 93 | >100 | 88 | >100 | >100 | 82 | 0 |
| 13h | 46 | 80 | 39 | >100 | 58 | >100 | >100 | >100 | 72 | 0 |
| 13i | >100 | >100 | >100 | 55 | >100 | >100 | >100 | >100 | 95 | 0 |
| 13j | 24 | — | >100 | — | >100 | >100 | >100 | — | 78 | 0 |
| 13k | 2.2 | 2.6 | 2.0 | 2.1 | 3.0 | 3.6 | 2.3 | 2.6 | 2.4 | ± |
| 19a | 0.70 | 1.4 | — | 0.99 | 3.7 | — | 0.36 | 10 | 3.2 | + |
| 19b | 8.7 | >100 | — | >100 | >100 | — | 5.1 | >100 | 45 | + |
| 20 | 9.4 | 2.0 | 3.1 | 0.42 | 6.7 | 2.1 | 4.1 | 17 | 5.0 | ± |
| 21 | 0.29 | 0.29 | — | 0.18 | 0.44 | — | 0.42 | 0.45 | 0.81 | ± |
| 22 | 0.36 | 0.34 | — | 0.38 | 1.7 | — | 0.77 | 1.4 | 0.98 | 0 |
| 23 | — | — | — | — | — | — | — | — | — | ± |
| 24 | >100 | >100 | >100 | — | >100 | >100 | >100 | >100 | 100 | 0 |
| 25 | 30 | 35 | 50 | — | 24 | 26 | 41 | 25 | 31 | 0 |
| 26 | 87 | 40 | — | 73 | >100 | 27 | 48 | >100 | 48 | ++ |
| 27 | 22 | 13 | 5.6 | — | 1.9 | 2.7 | 58 | 14 | 13 | ++ |

In general, most of the new indenoisoquinolines were even less cytotoxic in human cancer cell cultures than the moderately active (MGM 20 µM) lead compound 1. However, a few members of the series proved to be more cytotoxic than 1, including the N-allyl analog 13c (MGM 4.2 µM), the N-ethyl homolog 13k (MGM 2.4 µM), analog 19a (MGM 3.2 µM) having an N-(4'-hydroxybutyl) substituent, and the three dihydro derivatives 20 (MGM 5.0 µM), 21 (MGM. 0.81 µM), and 22 (MGM 0.98 µM). The N-ethylisoquinolinium species 27 (MGM 13 µM) and the relatively simple indenoisoquinolines 7 (MGM 16 µM) and 8 (MGM 14 µM), both lacking substituents on the aromatic rings, were slightly more cytotoxic than 1. Whereas the isoquinolinium salt 27 was comparable to 1 regarding topoisomerase I cleavage activity, the other more cytotoxic analogs were significantly less potent than 1 in the topoisomerase I cleavage assay.

The most potent of the new indenoisoquinolines vs. topoisomerase I proved to be 26 and 27 (Table 1). Both of these compounds were examined for induction of DNA cleavage in the 3'-end-labeled PvuII/HindIII fragment of pBluescript SK(-) phagemid DNA in the presence of topoisomerase I. The results were compared with those for the lead compound 1 and camptothecin (34). Some of the cleavage sites detected in the presence of 26, 27, and 1 were different from those induced by camptothecin (34). The indenoisoquinolines 26, 27, and 1 induced several topoisomerase cleavage sites that were not observed with camptothecin (34).

A wider array of compounds were tested at various concentrations and the topoisomerase inhibition data are summarized in Table 1. In general, except for 13k, which had very weak activity, the indenoisoquinolines induced similar cleavage patterns. With some of the compounds (e.g. 27), the activity seemed to increase initially as the concentration was increased, but then it declined at higher concentrations. This is reflected in FIG. 1, which was obtained after a more extensive investigation of the most potent indenoisoquinolines. The increase and following decrease in activity vs. concentration indicates that these compounds suppress topoisomerase-mediated DNA cleavage at higher drug concentrations, a result which is similar to the bell shaped curves seen with DNA unwinding or intercalating poisons. In order to investigate the possibility that some of the most potent indenoisoquinolines could be unwinding DNA and thus causing inhibition of topoisomerase activity at higher drug concentrations, they were examined for DNA unwinding activity. The unwinding assay using supercoiled DNA in the presence of topoisomerase I is a simple procedure to detect DNA intercalation. Our results show that the indenoisoquinoline 27 in fact does unwind DNA, as does 26 at higher concentrations. On the other hand, the indenoisoquinoline 19a, like the lead compound 1, does not appear to unwind DNA.

Camptothecin (34) induces DNA strand breaks by stabilizing the cleavage complexes and inhibiting DNA re-ligation. However, increasing salt concentration can reverse the camptothecin-induced cleavage complexes, and this method has been used to compare the molecular interactions between camptothecin derivatives and topoisomerase I cleavage complexes. The cleavage sites induced by camptothecin and the indenoisoquinoline derivatives 1,13c, 19a, 26, and 27 were reversed by salt treatment. This reversibility is consistent with the reversible trapping of topoisomerase cleavage complexes by the indenoisoquinolines.

In general, a planar indenoisoquinoline system appears to be a necessary, although not sufficient, condition for potent activity in the topoisomerase I cleavage assay. The nonplanar systems 20–25 were all inactive or displayed weak activity vs. topoisomerase I (Table 1). A direct comparison can be made between the planar indenoisoquinoline 1 and the corresponding non-planar, cis dihydro compound 20. Compound 1 displays good activity in the topoisomerase I cleavage assay, whereas the activity of 20 is weak. On the other hand, indenoisoquinolines 3–6 and 13f–13j are all planar ring systems that are inactive as topoisomerase I inhibitors.

It is of interest to compare the results obtained with the N-(4'-hydroxybutyl) compound 7 with the corresponding acid 26 in the topoisomerase I cleavage assay. Both of these simple indenoisoquinolines lack substituents in the aromatic rings and differ only in the oxidation state of the terminal carbon of the N-substituent. There is a significant increase in topoisomerase I inhibitory activity in going from the alcohol 7 to the corresponding carboxylic acid 26.

Table 2 shows the Pearson correlation coefficients derived from the $GI_{50}$ values for compound 1, camptothecin (34) and several camptothecin derivatives 33 and 30, as well as nitidine (28), fagaronine (29), the anticancer indenoisoquinolinium species 31 and 32, and several of the new indenoisoquinoline derivatives. The Pearson correlation coefficients quantify the degree of similarity in the cytotoxicity profiles of the compounds listed in the NCI panel of approximately 55 cancer cell lines. The analysis was performed using the COMPARE algorithm, which was developed to facilitate the rapid selection of compounds with similar or novel cytotoxicity profiles relative to established anticancer agents with known mechanisms of action. If the data pattern of an agent of interest correlates well with the data pattern of a known agent with a known mechanism of action, then the hypothesis is formed that the agent of interest may have the same mechanism of action as that of the known agent. In the present case, the dihydroindenoisoquinoline derivative 20 correlates well with the camptothecins 30, 33, and 34, suggesting that the cytotoxicity of 20 may be due to its topoisomerase I inhibitory activity.

TABLE 2

Pearson Correlations Derived From $GI_{50}$ Values.

| Cpd | 28 | 29 | 1 | 30 | 31 | 20 | 32 | 23 | 33 | 13k | 34 |
|---|---|---|---|---|---|---|---|---|---|---|---|
| 28 | 1.00 | 0.59 | 0.36 | 0.29 | 0.26 | 0.16 | 0.25 | 0.32 | 0.25 | 0.03 | 0.30 |
| 29 | 0.59 | 1.00 | 0.47 | 0.54 | 0.23 | 0.39 | 0.61 | 0.48 | 0.49 | -0.01 | 0.48 |
| 1 | 0.36 | 0.47 | 1.00 | 0.73 | 0.28 | 0.59 | 0.58 | 0.75 | 0.58 | 0.23 | 0.56 |
| 30 | 0.29 | 0.54 | 0.73 | 1.00 | 0.41 | 0.74 | 0.73 | 0.79 | 0.83 | 0.17 | 0.78 |
| 31 | 0.26 | 0.23 | 0.28 | 0.41 | 1.00 | 0.39 | 0.57 | 0.53 | 0.24 | 0.55 | 0.23 |
| 20 | 0.16 | 0.40 | 0.59 | 0.74 | 0.39 | 1.00 | 0.72 | 0.73 | 0.69 | 0.25 | 0.73 |

TABLE 2-continued

Pearson Correlations Derived From GI$_{50}$ Values.

| Cpd | 28 | 29 | 1 | 30 | 31 | 20 | 32 | 23 | 33 | 13k | 34 |
|-----|------|-------|------|------|------|------|------|------|------|------|------|
| 32  | 0.25 | 0.61  | 0.58 | 0.73 | 0.57 | 0.72 | 1.00 | 0.77 | 0.72 | 0.25 | 0.68 |
| 23  | 0.32 | 0.48  | 0.75 | 0.79 | 0.53 | 0.73 | 0.77 | 1.00 | 0.67 | 0.21 | 0.64 |
| 33  | 0.25 | 0.56  | 0.58 | 0.83 | 0.24 | 0.69 | 0.72 | 0.67 | 1.00 | 0.18 | 0.87 |
| 13k | 0.03 | −0.01 | 0.23 | 0.17 | 0.55 | 0.25 | 0.25 | 0.21 | 0.18 | 1.00 | 0.14 |
| 34  | 0.30 | 0.48  | 0.56 | 0.78 | 0.23 | 0.73 | 0.68 | 0.64 | 0.87 | 0.14 | 1.00 |

Since a number of topoisomerase I poisons also inhibit topoisomerase II, we tested the induction of topoisomerase II cleavage complexes by indenoisoquinolines. Our results show that compound 26 induced topoisomerase II cleavage complexes at sites which often did not overlap with the topoisomerase II sites induced by VP-16 (etoposide). Compound 27 had only marginal topoisomerase II activity at 100 $\mu$M and compounds 13c, 19a and 1 had no effect on topoisomerase II cleavage activity. Compounds 7 and 8 also exhibited weak topoisomerase II activity and compounds 13b, 13k, 20, 21 and 22 had no effect on topoisomerase II cleavage. These results indicate that the indenoisoquinolines are prominent topoisomerase I inhibitors, except for the two derivatives 26 and 27 that also produce DNA unwinding.

The objective of maximizing the cytotoxicity of indenoisoquinoline compounds against tumor or cancer cell lines was realized in the indenoisoquinolines 7, 8, 13e, 13k, 19a, 20, 21, 22, and 27, all of which displayed a lower MGM than the lead compound 1 (Table 1). Further, several topoisomerase I inhibitors were synthesized which rival the topoisomerase activity of 1, including 13c, 19a, 26, and 27. One obvious point of further interest is that with the possible exception of 19a, the two activities did not maximize in the same compounds, suggesting that the activity of some of the more cytotoxic compounds may not be due to their activity vs. topoisomerase. The situation is complicated by such factors as cellular uptake and possible conversion of parent compounds to metabolites which may have increased activity vs. topoisomerase I.

EXAMPLES

The following examples demonstrate the syntheses of several embodiments of the compounds of the present invention. Melting points were determined in capillary tubes and are uncorrected. Infrared spectra were obtained using CHCl$_3$ as the solvent unless otherwise specified. $^1$H NMR spectra were obtained using CDCl$_3$ as solvent and TMS as internal standard. $^1$H NMR spectra were determined at 300 MHz. Chemical ionization mass spectra (CIMS) were determined using isobutane as the reagent gas. Microanalyses were performed at the Purdue University Microanalysis Laboratory. Analytical thin-layer chromatography was carried out on Analtech silica gel GF 1000 micron glass plates. Compounds were visualized with short wavelength UV light or phosphomolybdic acid indicator. Silica gel flash chromatography was performed using 230–400 mesh silica gel.

Example 1

6-Ethyl-5,6-dihydro-5,11-diketo-11H-indeno[1,2-c] isoquinoline (3)

Ethylamine (0.2 mL, 3 mmol) was added to a stirred solution of benz[d]indeno[1,2-b]pyran-5, 11-dione (2) (0.49 g, 2 mmol) in CHCl$_3$ (10 mL). The bright orange mixture stirred overnight. To the reaction mixture CHCl$_3$ (100 mL) was added and the mixture washed with H$_2$O (3×25 mL) and brine (1×25 mL), dried (MgSO$_4$), and concentrated under reduced pressure to give an orange-red solid (0.43 g, 75%): mp 188–189° C.; IR (thin film) 2986, 1690, 1656, 1611, 1549, 1503, 1430, 1320, 1197, 991 cm$^{-1}$; $^1$H NMR (DMSO-d$_6$, 300 MHz) δ8.66 (d, 1H, J=8.3 Hz), 8.32 (d, 1H, J=7.9 Hz), 7.69 (dt, 1H, J=8.4, 1.4 Hz), 7.60 (dd, 1H, J=8.0, 1.4 Hz), 7.52 (d, 1H, J=6.9 Hz), 7.40 (m, 3H), 4.56 (q, 2H, J=7.2 Hz), 1.53 (t, 3H, J=7.2 Hz); CIMS, m/z (relative intensity) 276 (MH$^+$, 100). Anal. Calcd for C$_{18}$H$_{13}$NO$_2$: C, H, N.

Example 2

5,6-Dihydro-5,11-diketo-6-propyl-11H-indeno[1,2-c] isoquinoline (4)

Propylamine (0.3 mL, 3 mmol) was added to a stirred solution of benz[d]indeno[1,2-b]pyran-5,11-dione (2) (0.49 g mmol) in CHCl$_3$ (10 mL). The red solution stirred overnight before CHCl$_3$ (75 mL) was added and the mixture washed with H$_2$O (3×20 mL) and brine (1×20 mL), dried (MgSO$_4$), and concentrated under reduced pressure to give a yellow-orange solid (0.32 g, 55%): mp 166–167° C.; IR (neat) 2967, 1660, 1502, 1427, 1317, 1193, 959 cm$^{-1}$; $^1$H NMR (CDCl$_3$, 300 MHz) δ8.69 (d, 1H, J=8.0 Hz), 8.33 (d, 1H, J=9.0 Hz), 7.70 (td, 1H, J=9.0, 3.0 Hz), 7.62 (d, 1H, J=6.2 Hz), 7.40 (m, 4H), 4.46 (t, 2H, J=8.0 Hz), 1.92 (m, 2H), 1.12 (t, 3H, J=7.4 Hz); CIMS m/z (relative intensity) 290 (MH+, 100). Anal. Calcd for C$_{19}$H$_{15}$NO$_2$: C, H, N.

Example 3

6-Cyclopropyl-5,6-dihydro-5,11-diketo-11H-indeno [1,2-c]isoquinoline (5)

Cyclopropylamine (10 mL) was added to a stirred solution of benz[d]indeno[1,2-b]pyran-5,11-dione (2) (0.28 g, 1.1 mmol) in CHCl$_3$ (10 mL). The red solution stirred overnight before CHCl$_3$ (50 mL) was added and the mixture washed with H$_2$O (3×20 mL) and brine (1×20 mL), dried (MgSO$_4$), and concentrated under reduced pressure to give a red solid (0.3 g, 91%): mp 206–208° C.; IR (thin film) 3751, 1665, 1500, 1420, 1311, 1083, 950 cm$^{-1}$; $^1$H NMR (CDCl$_3$, 300 MHz) δ8.62 (d, 1H, J=7.7 Hz), 8.29 (d, 1H, J=8.4 Hz), 7.88 (d, 1H, J=7.0 Hz), 7.69 (td, 1H, J=6.9, 1.2 Hz), 7.59 (dd, 1H, J=6.1, 1.3 Hz), 7.40 (m, 3H), 3.37 (m, 1H), 1.45 (q, 2H, J=6.8 Hz), 0.99 (m, 2H); CIMS m/z (relative intensity) 288 (MH$^-$, 100). Anal. Calcd for C$_{19}$H$_{13}$NO$_2$: C, H, N.

Example 4

5,6-Dihydro-5,11-diketo-6-(methoxycarbonylmethyl)-11H-indeno[1,2-c] isoquinoline (6)

Triethylamine (2.7 mL, 19.4 mmol) was added to a stirred solution of glycine methyl ester hydrochloride (1.57 g, 12.5 mmol) in chloroform (30 mL). After 1 h, benz[d]indeno[1,2-b]pyran-5,11-dione (2) (1.24 g, 5.0 mmol) was added to the mixture. The red mixture stirred an additional 4 h before $CHCl_3$ (100 mL) was added and the mixture washed with $H_2O$ (3×50 mL) and brine (1×50 mL), dried ($MgSO_4$), and concentrated under reduced pressure to give an orange-red solid (1.48 g, 92%): mp 248–251° C.; IR (thin film) 2956, 1735, 1667, 1609, 1502, 1426, 1227, 981 cm$^{-1}$; $^1$H NMR ($CDCl_3$, 300 MHz) δ8.68 (d, 1H, J=8.0 Hz), 8.32 (d, 1H, J=8.2 Hz), 7.73 (td, 1H, J=7.1, 1.3 Hz), 7.61 (m, 1H), 7.47 (td, 1H, J=7.1, 1.1 Hz), 7.37 (m, 2H), 7.26 (m, 1H), 5.34 (s, 2H), 3.79 (s, 3H); CIMS m/z (relative intensity) 320 (MH$^+$, 100). Anal. Calcd for $C_{19}H_{13}NO_4$: C, H, N.

Example 5

5,6-Dihydro-6-(4-hydroxy-1-butyl)-5,11-diketo-11H-indeno[1,2-c]isoquinoline (7)

4-Amino-1-butanol (0.891 g, 10 mmol) was added to a chloroform (30 mL) solution of benz[d]indeno[1,2-b]pyran-5,11-dione (2) (2.48 g, 10 mmol) and the reaction mixture was stirred at room temperature 2 days. The reaction mixture turned dark red. The reaction mixture was taken in chloroform (100 mL) and washed with water (2×50 mL), 0.5 N HCl (50 mL), brine (100 mL) and dried ($Na_2SO_4$) and concentrated to give the crude product. The product was filtered through a short column of silica gel and the polar fraction concentrated to afford a reddish brown solid which was crystallized from isopropanol to yield the product (2.56 g, 80%): mp 160–162° C.; IR (KBr) 3300, 1695, 1645, 1615 cm$^{-1}$; $^1$H NMR ($CDCl_3$) δ8.63 (d, J=8.1 Hz, 1H), 8.26 (d, J=8.1 Hz, 1H), 7.70–7.15 (m, 6H), 4.51 (t, J=7.8 Hz, 2H), 3.77 (t, J=6.1 Hz, 2H), 1.99 (p, J=8.0 and 7.5 Hz, 2H), 1.83 (s, 1H, $D_2O$ exchangeable). Anal. Calcd for $C_{20}H_{17}NO_3$ C, H, N.

Example 6

5,6-Dihydroxy-6-(5-hydroxy-1-pentyl)-5,11-diketo-11H-indeno[1,2-c]isoquinoline (8)

5-Amino-1-pentanol (1.03 g, 10 mmol) was added to a chloroform (20 mL) solution of benz[d]indeno[1,2-b]pyran-5,11-dione (2) (2.48 g, 10 mmol) and the reaction mixture was stirred at room temperature overnight. The reaction mixture turned dark red. The reaction mixture was taken in chloroform (100 mL) and washed with water (2×50 mL), 0.5 N HCl (50 mL), brine (100 mL) and dried ($Na_2SO_4$) and concentrated to give the crude product. The TLC showed traces of starting material. The product was filtered through a short column of silica gel and the polar fraction concentrated to get a reddish brown solid which was crystallized from isopropanol to afford the product (2.53 g, 76%): mp 146–148° C.; IR (KBr) 2996, 1698, 1642, 1615 cm$^{-1}$; $^1$H NMR ($CDCl_3$) δ8.63 (d, J=8.1 Hz, 1H), 8.27 (d, J=8.1 Hz, 1H), 7.67 (d, J=8.4 Hz, 1H), 7.56 (d, J=6.8 Hz, 1H), 7.45–7.30 (m, 4H), 4.47 (t, J=7.9 Hz, 2H), 3.71 (t, J=5.9 Hz, 2H), 1.92 (p, J=7.9 and 7.4 Hz, 2H), 1.82 (s, 1H, $D_2O$ exchangeable), 1.78–1.55 (m, 4H); CIMS m/z (relative intensity) 334 (MH$^+$, 100). Anal. Calcd for $C_{21}H_{19}NO_3$: C, H, N.

Example 7 cis-4-Carboxy-3,4-dihydro-N-methyl-3-(3',4'-methylenedioxyphenyl)-1(2H)isoquinolone (12a)

Homophthalic anhydride (10 a) (0.81 g, 5 mmol) was added to a stirred solution of 3,4-ethylenedioxybenzylidenemethylamine (11a) (0.82 g, 5 mmol) in chloroform (5 mL). After 30 min, the precipitated product was filtered from the yellow solution and washed with chloroform to give a pale yellow solid (1–2 g, 74%): mp 165–167° C.; $^1$H NMR (DMSO-$d_6$) δ7.99 (d, J=7.5 Hz, 1H), 7.48 (m, 3H), 6.76 (d, J=8.0 Hz, 1H), 6.52 (d, J=8.0 Hz, 1H), 6.43 (s, 1H), 5.93 (s, 2H), 5.03 (d, J=6.2 Hz, 1H), 4.64 (d, J=6.1 Hz, 1H), 2.89 (s, 3H); CIMS m/z (relative intensity) 326 (MH$^+$, 100).

Example 8

5,6-Dihydro-5,11-diketo-6-methyl-8,9-methylenedioxy-11H-indeno[1,2-c]isoquinoline (13a)

Thionyl chloride (8.1 mL) was added with stirring to the cis acid 12a (0.7 g, 2.1 mmol). The yellowish-brown mixture became orange within 15 min and after 30 min was red. After 4 h, the reaction mixture was diluted with benzene (25 mL) and evaporated to dryness. The brownish-red solid was recrystallized from methanol and passed through a short column ($SiO_2$) and eluted with chloroform to give a brown solid (0.14 g, 24%): mp 310–312° C.; IR (thin film) 2358, 1652,1540,1506,1292 cm$^{-1}$; $^1$H NMR (DMSO-$d_6$) δ8.43 (d, J=8.0 Hz, 1H), 8.16 (d, J=8.0 Hz, 1H), 7.75 (t, J=7.5 Hz, 1H), 7.56 (s, 1H), 7.44 (t, J=7.6 Hz, 1H), 7.15 (s, 1H), 6.19 (s, 2H), 3.92 (s, 3H); CIMS m/z (relative intensity) 306 (MH+, 100). Anal. Calcd for $C_{18}H_{11}NO_4$: C, H, N.

Example 9

3,4-Methylenedioxybenzylidenebutylamine (11b)

Piperonal (7.5 g, 50 mmol) and n-butylamine (6 mL, 75 mmol) were stirred in chloroform (100 mL) in the presence of anhydrous $MgSO_4$ (5 g) at room temperature for 4 h. The mixture was filtered and the residue was washed with chloroform (20 mL). The combined filtrate was concentrated under reduced pressure to afford a yellow oil (9.8 g, 96%): IR (neat) 1649, 1643, 1604 cm$^{-1}$; $^1$H NMR ($CDCl_3$) δ8.11 (s, 1H), 7.31 (d, J=1.2 Hz, 1H), 7.06 (dd, J=1.2 and 7.9 Hz, 1H), 6.79 (d, J=7.8 Hz, 1H), 5.95 (s, 2H), 3.53 (t, J=6.6 Hz, 2H), 1.63 (p, J=7.3 Hz, 2H), 1.37 (hextet, J=7.3 Hz, 2H), 0.91 (t, J=7.3 Hz, 3H).

Example 10 cis-N-(1-Butyl)-4-carboxy-3,4-dihydro-3-(3',4'-methylenedioxyphenyl)-1(2H)-isoquinolone (12b)

Homophthalic anhydride (10a) (3.24 g, 20 mmol) was added to a chloroform (20 mL) solution of the imine 11b (4.1 g, 20 mmol) and the mixture was stirred at room temperature for 45 min, after which the TLC showed the complete disappearance of the starting materials. The reaction mixture was concentrated to remove chloroform completely. The residue was dissolved in hot ethyl acetate (100 mL) and left at room temperature for 12 h. The colorless crystals that separated were filtered and dried to give pure 12b (6.57 g, 89%): mp 178–181° C.; IR (KBr) 1712, 1634, 1600 cm$^{-1}$; $^1$H NMR ($CDCl_3$) δ8.08 (dd, J=1.0 and 7.5 Hz, 1H), 7.52 (d, J=7.5 Hz, 1H), 7.40–7.28 (m, 2H), 6.51–6.45 (m, 2H), 6.37 (s, 1H), 5.75 (dd, J=1.1 and 6.4 Hz, 2H), 4.87 (d, J=6.2 Hz, 1H), 4.51 (d, J=6.2 Hz, 1H), 3.93 (dt, J=7.2 and 6.6 Hz, 1H), 2.73 (dt, J=7.2 and 6.6 Hz, 1H), 1.52 (p, J=7.2 Hz, 2H), 1.26 (hextet, J=7.3) Hz, 2H), 0.83 (t, J=7.2 Hz, 3H); CIMS m/z (relative intensity) 368 (MH$^+$, 100); EIMS m/z (relative intensity) 367 (M$^+$, 5), 322 (30), 135 (100). Anal. Calcd for $C_{21}H_{21}NO_5$: C, H, N.

Example 11

6-(1-Butyl)-5,6-dihydro-5,11-diketo-8,9-methylenedioxy-11H-indeno[1,2-c]isoquinoline (13b)

Thionyl chloride (30 mL) was added dropwise to the acid 12b (3.35 g, 0.089 ml) with stirring. The resulting solution was stirred at room temperature for 12 h, after which the solution turned dark pink. Benzene (20 mL) was added to the reaction mixture and it was concentrated under reduced pressure. The resulting residue was purified by column chromatography (acetone:hexane, 1:4) followed by crystallization (EtOAc/Hexane) to obtain pure indenoisoquinoline 13b (1.37 g, 44%): mp 200–201° C.; IR (KBr) 1691, 1665, 1631 cm$^{-1}$; $^1$H NMR (CDCl$_3$) δ8.50 (d, J=8.1 Hz, 1H), 8.21 (d, J=8 Hz, 1H), 7.61 (t, J=8 Hz, 1H), 7.34 (t, J=8 Hz, 1H), 6.98 (s, 1H), 6.87 (s, 1H), 6.03 (s, 2H), 4.34 (t,J=8 Hz, 2H), 1.80 (p, J=8 Hz, 2H), 1.51 (hextet, J=8 Hz, 2H), 1.01 (t, J=8 Hz, 3 Hz); $^{13}$C NMR (CDCl$_3$) δ189.01, 163.1, 154.85, 151.21, 148.97, 133.58, 132.18, 132.05, 130.50, 128.29, 126.39, 122.82, 122.69, 107.48, 105.12, 104.84, 102.57, 44.13, 31.33, 20.1, 13.73; CIMS m/z (relative intensity) 348 (MH$^+$, 100); EIMS m/z (relative intensity) 347 (M$^+$, 60), 330 (10), 318 (30), 291 (100). Anal. Calcd for C$_{21}$H$_{17}$NO$_4$: C, H, N.

Example 12

3,4-Dimethoxybenzylideneallylamine (11c)

Allylamine (6 mL, 80 mmol) was added to a solution of 3,4-dimethoxybenzaldehyde (8.3 g, 50 mmol) in dichloromethane (50 mL) in the presence of anhydrous magnesium sulfate (5 g) and the reaction mixture was stirred at room temperature overnight. The reaction mixture was filtered, the residue washed with chloroform (10 mL) and the combined filtrate was concentrated under reduced pressure to afford 11 as a yellow oil (10.18 g, 99%): IR (neat) 1692, 1679, 1646, 1604 cm$^{-1}$; $^1$H NMR (CDCl$_3$) δ8.14 (s, 1H), 7.40 (d, J=1.8 Hz, 1H), 7.11 (dd, J=1.8 and 8 Hz, 1H), 6.82 (d, J=8 Hz, 1H), 6.10–5.90 (m, 1H), 5.20 (dd, J=1.8 and 17.4 Hz, 1H), 5.10 (dd, J=1.3 and 10 Hz, 1H), 4.20 (d, J=6.3 Hz, 2H), 3.88 (s, 3H), 3.85 (s, 3H).

Example 13 cis-N-Ally-4-carboxy-3,4-dihydro-6,7-dimethoxy-3-(3',4'-methylenedioxy phenyl)-1(2H)isoquinolone (12c)

4,5-Dimethoxyhomophthalic anhydride (10b) (1.11 g, 5 mmol) was added to a chloroform (10 mL) solution of the imine 11c (0.945 g, 5 mmol) and the mixture was stirred at room temperature for 45 min, after which the TLC showed the complete disappearance of the starting materials and a white precipitate formed in the reaction mixture. The precipitated product was filtered off and washed with chloroform (5 mL) and dried to give pure 12c (1.43 g, 70%): mp 235–238° C.; IR (KBr) 3000, 1736, 1686, 1615 cm$^{-1}$; $^1$H NMR (DMSO-d$_6$) δ13.0 (bs, 1H), 7.52 (s, 1H), 7.13 (s, 1H), 6.76 (d, J=8.5 Hz, 1H), 6.52 (d, J=8.5 Hz, 1H), 6.44 (s, 1H), 5.94 (s, 2H), 5.85–5.70 (m, 1H), 5.16 (dd, J=3.5 & 17.5 Hz, 2H), 4.92 (d, J=6.5 Hz, 1H), 4.57 (d, J=6.5 Hz, 1H), 3.82 (s, 3H), 3.75 (s, 3H), 3.20–3.10 (m, 2H). CIMS m/z (relative intensity) 412 (MH$^+$, 100). Anal. Calcd for C$_{22}$H$_{21}$NO$_7$: C, H, N.

Example 14

6-Allyl-2,3-dimethoxy-5,6-dihydro-5,11-oxo-8,9-(methylenedioxy)-11H-indeno[1,2-c]isoquinoline (13c)

Treatment of 12c (2.05 g, 5 mmol) with Eaton's reagent (10% P$_2$O$_5$, in methanesulfonic acid, 60 mL) at room temperature with stirring in an open flask for 24 h resulted in a mixture of 22 and 13c. The two products were separated by column chromatography on silica gel (230–400 mesh) using hexane:acetone (4:1) to afford 22 (842 mg, 43%) and 12c as a purple solid product (588 mg, 30%) after recrystallization from ethyl acetatehexane: mp 290–294° C.; IR (KBr) 2370, 1698, 1653, 1551, 1484; $^1$H NMR (CDCl$_3$) δ7.97 (s, 1H), 7.63 (s, 1H), 6.99 (s, 1H), 6.91 (s, 1H), 6.20–6.05 (m, 1H), 6.06 (s, 2H, 5.31 (d, J=10.5 Hz, 1H), 5.20–5.00 (m, 3H), 3.33 (s, 3H), 3.97 (s, 3H). Anal. Calcd for C$_{22}$H$_{17}$NO$_6$: C, 67.52; H, 4.38; N, 3.58. Found: C, 67.18; H, 4.32; N, 3.31.

Example 15 cis-N-(1-Butyl)-4-carboxy-3,4-dihydro-6,7-dimethoxy-3-(3',4'methylenedioxyphenyl)-1(2H) isoquinolone (12d)

4,5-Dimethoxyhomophthalic anhydride 10b (2.22 g, 10 mmol) was added to a chloroform (10 mL) solution of the imine (11b) (2.1 g, 10 mmol) and the mixture was stirred at room temperature for 45 min, after which the TLC showed the complete disappearance of the starting materials and a white precipitate formed in the reaction mixture. The precipitated product was filtered off and washed with chloroform (5 mL) and dried to give pure 12d (3.45 g, 81%): mp 242–244° C.; IR (KBr) 1732, 1640, 1610, 1600 cm$^{-1}$; $^1$H NMR (CDCl$_3$+DMSO-d$_6$) δ7.56 (s, 1H), 7.08 (s, 1H), 6.55–6.48 (m, 2H), 6.40 (s, 1H), 5.79 (d, J=2.5 Hz, 2H), 4.86 (d, J=6.2 Hz, 1H), 4.45 (d, J=6.2 Hz, 1H), 3.88 (dt, J=7.4 and 6.1 Hz, 1H), 2.71 (dt, J=7.5 and 6.1 Hz, 1H), 1.49 (p, J=7.3 Hz, 2H), 1.26 (hextet, J=7.3 Hz, 2H), 0.83 (t, J=7.3 Hz, 3H). Anal. Calcd for C$_{23}$H$_{25}$NO$_7$,: C, H, N.

Example 16

6-(1-Butyl)-5,6-dihydro-5,11-diketo-2,3-dimethoxy-8,9-methylenedioxy11H-indeno[1,2-c]isoquinoline (13d)

Thionyl chloride (30 mL) was added dropwise to the acid 12d (2.135 g, 5 mmol) with stirring. The resulting solution was stirred at room temperature for 12 h after which the solution turned dark pink. Benzene (20 mL) was added to the reaction mixture and it was concentrated under reduced pressure. Benzene (50 mL) was added to the resulting residue and the pink solid was filtered off to obtain pure indenoisoquinoline 13d (1.3 g, 65%): mp 280–284° C.; IR (KBr) 1699, 1653, 1646, 1578 cm$^{-1}$; $^1$H NMR (CDCl$_3$) δ7.99 (s, 1H), 7.62 (s, 1H), 7.04 (s, 1H), 6.92 (s, 1H), 6.07 (s, 2H), 4.39 (t, J=7.6 Hz, 2H), 4.01 (s, 3H), 3.96 (s, 3H), 1.82 (p, J=7.3 Hz, 2H), 1.68–1.55 (m, 2H), 1.02 (t, J=7.3 Hz, 3 Hz). Anal. Calcd for C$_{23}$H$_{21}$NO$_6$ 0.1 H$_2$O: C, H, N.

Example 17

3,4-Methylenedioxybenzylidenebenylamine (11e)

Piperonal (4.5 g, 30 mmol) and benzylamine (3.21 g, 30 mmol) were stirred in methylene chloride (30 mL) in the presence of anhydrous MgSO$_4$ (5 g) at room temperature for 4 h. The mixture was filtered and the residue was washed with methylene chloride (20 mL) and the combined filtrate was concentrated under reduced pressure to afford a white solid (7.03 g, 98%): mp 69–70° C.; IR (KBr) 1638, 1618, 1602 cm$^{-1}$; $^1$H NMR (CDCl$_3$) δ8.18 (s, 1H), 7.33 (d, J=1.3 Hz, 1H), 7.30–7.10 (m, 5H), 7.06 (dd, J=1.3 and 8.0 Hz, 1H), 6.74 (d, J=8 Hz, 1H), 5.90 (s, 2H), 4.69 (s, 2H).

Example 18 cis-N-Benzyl-4-carboxy-3,4-dihydro-6,7-dimethoxy-3-(3',4'-methylenedioxyphenyl)-1(2H)isoquinolone (12e)

4,5-Dimethoxyhomophthalic anhydride (10b) (1.11 g, 5 mmol) was added to a chloroform (10 mL) solution of the imine 11e (1.19 g, 5 mmol) and the mixture was stirred at room temperature for 2 h, after which the TLC showed the complete disappearance of the starting materials and a white precipitate formed in the reaction mixture. The precipitated product was filtered off and washed with chloroform (5 mL) and dried to give pure 12e (1.89 g, 82%): mp 262–264° C.; IR (KBr) 1736, 1654, 1647, 1618, 1595, 1575 cm$^{-1}$; $^1$H NMR (DMSO-d$_6$) δ7.56 (s, 1H), 7.35–7.20 (m, 5H), 7.13 (s, 1H), 6.75 (d, J=8.3 Hz, 1H), 6.51 (d, J=8.1 Hz, 1H), 6.43 (s, 1H), 5.93 (s, 2H), 5.25 (d, J=15.6 Hz, 1H), 4.86 (d, J=5.6 Hz, 1H), 4.51 (d, J=5.3 Hz, 1H), 3.83 (s, 3H), 3.74 (s, 3H), 3.39 (d, J=15.6 Hz, 1H).

Example 19

6-Benzyl-5,6-dihydro-5,11-diketo 2,3-dimethoxy-8,9-methylenedioxy-11H-indeno[1,2-c]isoquinoline (13e)

Thionyl chloride (10 mL) was added dropwise to the acid 12e (1.15 g, 1.5 mmol) with stirring. The resulting mixture was stirred at room temperature for 5 h, after which the solution turned purple. Benzene (20 mL) was added to the reaction mixture and it was concentrated under reduced pressure. Carbon tetrachloride was added to the resulting residue and the undissolved solid was filtered off to obtain pure indenoisoquinoline 13e (0.716 g, 65%): mp 310–312° C.; IR (KBr) 1695, 1652, 1619, 1578 cm$^{-1}$; $^1$H NMR (CDCl$_3$) δ8.02 (s, 1H), 7.66 (s, 1H), 7.4–7.20 (m, 5H), 7.02 (s, 1H), 6.74 (s, 1H), 5.99 (s, 2H), 5.69 (s, 2H), 4.04 (s, 3H), 3.97 (s, 3H); $^{13}$C NMR (CDCl$_3$) δ162.54, 155.03, 148.72, 135.44, 132.52, 130.22, 129.19, 127.67, 125.64, 108.32, 105.24, 103.03, 102.47, 56.31, 47.80 and 56.03. Anal. Calcd for C$_{26}$H$_{19}$NO$_6$ 0.8 H$_2$O: C, H, N.

Example 20

3,4-Methylenedioxybenzylidene-p-anisidine (11f)

Piperonal (15 g, 0.1 mol) and p-anisidine (12.3 0.1 mol) were stirred in methylene chloride (100 mL) in the presence of anhydrous MgSO$_4$, (5 g) at room temperature for 4 h. The mixture was filtered, the residue was washed with methylene chloride (20 mL), and the combined filtrate was concentrated under reduced pressure to afford a yellow solid. The crude product was crystallized in 95% ethanol to give white crystalline solid (22.38 g, 87%): mp 113–114° C.; IR (KBr) 1636 and 1617 cm$^{-1}$; $^1$H NMR (CDCl$_3$) δ8.33 (s, 1H), 7.51 (d, J=1.2 Hz, 1H), 7.25–7.10 (m, s), 6.95–6.8 (m, 3H), 6.01 (s, 2H), 3.80 (s, 3H).

Example 21 cis-N-(p-Anisyl)-4-carboxy-3,4-dihydro-6,7-dimethoxy-3-(3',4'-methylene-dioxyphenyl)-1(2H)isoquinolone (12f)

4,5-Dimethoxyhomophthalic anhydride (10b) (1.11 g, 5 mmol) was added to a chloroform (10 mL) solution of the imine 11f (1.275 g, 5 mmol) and the mixture was stirred at room temperature for 12 h, after which the TLC showed the complete disappearance of the starting materials and a white precipitate formed in the reaction mixture. The precipitated product was filtered off, washed with chloroform (5 mL), and dried to afford pure 12f (1.36 g, 60%): mp>350° C.; IR (KBr) 1644, 1639, 1599 cm$^{-1}$; $^1$H NMR (DMSO-d$_6$,) δ7.60–7.30 (m, 5H), 7.20–6.80 (m, 4H), 6.10 (s, 2H), 5.30 (d, J=6 Hz, 1H), 4.77 (d, J=6 Hz, 1H), 3.78 (s, 3H), 3.71 (s, 3H), 3.01 (s, 3H).

Example 22

6-(p-Anisyl)-2,3-dimethoxy-5,6-dihydro-5,11-diketo-8,9-methylenedioxy-11H-indeno[1,2-c]isoquinoline (13f)

Thionyl chloride (9mL) was added dropwise to the acid 12f (0.822 g, 2 mmol) with stirring. The resulting solution was stirred at room temperature for 5 h, after which the solution turned purple. Benzene (20 mL) was added to the reaction mixture and it was concentrated under reduced pressure. The resulting residue was passed through a short column of silica gel (230–400 mesh) eluting with chloroform. Concentration of the eluent resulted in a pink solid which was crystallized from ethyl acetate to obtain pure indenoisoquinoline 13f (0.436 g, 53%): mp 360–364° C.; IR (KBr) 1692, 1652, 1625 and 1552 cm$^-$; $^1$H NMR (CDCl$_3$) δ7.94 (s, 1H), 7.60 (s, 1H), 7.34 (d, J=8.1 Hz, 2H), 7.24 (s, 1H), 7.10 (d, J=8 Hz, 2H), 6.88 (s, 1H), 5.90 (s, 2H), 5.05 (s, 1H), 4.02 (s, 3H), 3.93 (s, 3H), 3.91 (s, 3H); CIMS m/z (relative intensity) 458 (MH$^+$, 100). Anal. Calcd for C$_{26}$H$_{19}$NO$_7$: C, H, N.

Example 23

3,4-Dibenzyloxybenzylidenemethylamine (11g)

3,4-Dibenzyloxybenzaldehyde (7.96 g, 25.0 mmol) was added to a 40% aqueous solution of methylamine (10 mL) and the reaction mixture was stirred at room temperature for 3 h. The mixture was extracted with ether (4×75 mL), the ether layers were combined, and the solution washed with saturated aqueous sodium chloride (75 mL), dried (MgSO$_4$), and concentrated under reduced pressure to give an off-white solid (7.7 g, 94%): mp 56–57° C.; IR (KBr) 3031, 2936, 2832, 1648, 1600, 1582, 1509, 1454, 1431, 1267, 1171, 113 7, 1017, 735, 696 cm$^{-1}$; $^1$H NMR (CDCl$_3$, 300 MHz) δ8.14 (s, 1H), 7.35 (m, 11H), 7.11 (dd, J=8.1, 1.0 Hz, 1H), 6.93 (d, J=8.1 Hz, 1H), 5.18 (s, 4H), 3.46 (s, 3H); CIMS m/z (relative intensity) 332 (MH$^+$, 100). Anal. Calcd for C$_{31}$H$_{21}$NO$_2$: C, H, N.

Example 24 cis-3-(3',4'-Dibenzyloxyphenyl)-4-carboxy-3,4-dihydro-N-methyl-1-2H-isoquinolone (12g)

Homophthalic anhydride (10a) (0.81 g, 5 mmol) was added to a stirred solution of 3,4-dibenzyloxybenzylidenemethylamine (11g) (1.66 g, 5 mmol) in chloroform (5 mL). After 30 min, ether was added and the resulting precipitate was filtered and washed with ether to give a pale yellow solid (0.9 g, 36%): mp 170–172° C.; IR (thin film) 3030, 1731, 1625, 1514, 1263, 1137, 1014 cm$^{-1}$; $^1$H NMR (CDCl$^3$, 300 MHz) δ8.19 (dd, J=6.5, 1.9 Hz, 1H), 7.36 (m, 10H), 7.09 (d, J4.9, 1H), 6.74 (d, J=8.9, 1H), 6.68 (d, J=8.9, 1H), 6.51 (m, 2H), 5.03 (d, J=7.2, 2H), 4.92 (d, J 6.1, 2H), 4.8 (d, J=6.3, 2H), 4.5 (d, J=6.2, 2H), 2.98 (s, 3H); CIMS m/z (relative intensity) 494 (MH$^+$, 100). Anal. Calcd for C$_{31}$H$_{27}$NO$_5$: C, H, N.

Example 25

8,9-Dibenzyloxy-5,6-dihydro-5,11-diketo-6-methyl-11H-indeno[1,2-c]isoquinoline (13g)

Thionyl chloride (8.1 mL) was added with stirring to the cis acid 12g (0.7 g, 2.1 mmol). The result was a yellowish-brown mixture that became orange within 15 min and after 30 min was red. After 4 h, the reaction mixture was diluted with benzene (25 mL) and evaporated to dryness. The brownish-red solid was recrystallized from methanol and passed through a short column ($SiO_2$), eluting with chloroform, to give a brown solid (0.14 g, 24%): MP 198–200° C.; $^1$H NMR (DMSO-$d_6$) δ8.43 (d, J=8.0 Hz, 1H), 8.16 (d, J=8.0 Hz, 1H), 7.75 (t, J=7.5 Hz, 1H), 7.39 (m, 13H), 5.34 (s, 1H), 5.29 (s, 1H), 3.93 (s, 1H); CIMS m/z (relative intensity) 474 ($MH^+$, 100). Anal. Calcd for $C_{31}H_{23}NO_4$: C, H, N.

Example 26 cis-3-(3',4'-Dibenzyloxyphenyl)-4-carboxy-3,4-dihydro-N-methyl-6,7-dimethoxy-1-(2H)-isoquinolone (12h)

3,4-Dimethoxyhomophthalic anhydride (10b) (0.56 g, 2.5 mmol) was added to a stirred solution of 3,4-dibenzyloxy benzylidenemethylamine (11g) (0.83 g, 2.5 mmol) in chloroform (3 mL). After 30 min, the yellow mixture became heterogeneous and ether was added to further precipitate the product. The light yellow precipitate was collected and washed with chloroform to give a solid (0.59 g, 44%): mp 194–196° C.; $^1$H NMR (CDCl$_3$) δ7.49 (s, 1H), 7.34 (m, 11H), 7.18 (s, 1H), 6.91 (d, 1H, J=8.3 Hz), 6.79 (s, 1H), 6.57 (d, 1H, J=8.3 Hz), 5.02 (s, 2H), 4.98 (d, 1H, J=6.1 Hz), 4.92 (s, 2H), 4.50 (d, 1H, J=5.8 Hz), 3.78 (s, 3H), 3.74 (s, 3H), 2.81 (s, 3H); FABMS (m-NBA) m/z (relative intensity) 554 ($MH^+$, 100).

Example 27

8,9-Dibenzyloxy-5,6-dihydro-5,11-diketo-6-methyl-2,3-dimethoxy-11H-indeno[1,2-c]isoquinoline (13h)

Thionyl chloride (15 mL) was added with stirring to the cis acid 12h (1.2 g, 2.2 mmol). The result was an orange mixture that became dark red within 15 min. After 6 h, the reaction mixture was diluted with benzene (25 mL) and evaporated to dryness. Chloroform (7 mL) was added to the purple solid and the solid was collected and washed with ether to give a light purple solid (0.75 g, 64%): mp 238–240° C.; IR (thin film) 3027, 2963, 1685, 1649, 1493, 1458, 1252, 1203, 1088, 1014 cm$^{-1}$; $^1$H NMR (CDCl$_3$, 300 MHz) δ7.96 (s, 1H), 7.62 (s, 1H), 7.38 (m, 1H), 7.21 (s, 1H), 7.11 (s, 1H), 5.23 (d, 4H, J=5.2 Hz), 4.02 (s, 3H) 3.95 (s, 3H), 3.81 (s, 3H); CIMS m/z (relative intensity) 534 ($MH^+$, 22). Anal. Calcd for $C_{33}H_{27}NO_6$: C, H, N.

Example 28

3,4,5-Trimethoxybenzylidenemethylamine (11i)

3,4,5-Trimethoxybenzaldehyde (7.81–40.0 mmol) and a 40% aqueous solution of methylamine (20 mL) were stirred at room temperature for 2.5 h. The mixture was extracted with ether (4×75 mL), the ether layers were combined, and the solution washed with saturated aqueous sodium chloride (75 mL), dried (MgSO$_4$), and concentrated under reduced pressure to give a colorless oil (7.94 g, 95%): IR (neat) 2940, 2840, 1646, 1576, 1500, 1453, 1407, 1369, 1323, 1230, 1115, 1013 cm$^{-1}$; $^1$H NMR (CDCl$_3$, 300 MHz) δ8.18 (d, 1H, J=1.3 Hz), 6.95 (s, 2H), 3.89 (s, 6H), 3.87 (s, 3H), 3.50 (d, 3H, J=1.3 Hz); CIMS m/z (relative intensity) 210 ($MH^+$, 100). Anal. Calcd for $C_{11}H_{15}NO_3$: C, H, N.

Example 29 cis-4-Carboxy-3,4-dihydro-N-methyl-6,7-dimethoxy-3-(3',4',5'-trimethoxyphenyl)-1 (2H) isoquinolone (12i)

3,4-Dimethoxyhomophthalic anhydride (10b) (0.22 g, mmol) was added to a stirred solution of 3,4,5-trimethoxybenzylidenemethylamine (11i) (0.23 g, 1 mmol) in chloroform (5 mL). After 30 min, the bright yellow homogeneous solution was tan and no solid was observed. Ether was added dropwise and the resulting precipitate was filtered and washed with ether to give fine white solid (0.1 g, 20%): mp, 229–231° C.; IR (neat) 2928, 1743, 1593, 1418, 1329, 1241, 1167, 1119 cm$^{-1}$; $^1$H NMR (CDCl$_3$, 300 MHz) δ7.50 (s, 1H), 7.15 (s, 1H), 6.38 (s, 2H), 5.0 (d, 1H, J=5.9 Hz), 4.48 (d, 1H, J=5.9 Hz), 3.79 (s, 3H), 3.72 (s, 3H), 3.59 (s, 9H); CIMS m/z (relative intensity) 432 ($MH^+$, 100). Anal. Calcd for $C_{22}H_{25}NO_8$: C, H, N.

Example 30

5,6-Dihydro-5,11-diketo-6methyl-2,3,8,9,10-pentamethoxy-11H-indeno[1,c]isoquinoline (13i)

Thionyl chloride (15 mL) was added with stirring to the cis acid 12i (1.2 g 2.8 mmol). The result was a yellow mixture that became dark red within 15 min. After 4 h, the reaction mixture was diluted with benzene (25 mL) and evaporated to dryness. The purple solid was dissolved in chloroform and ether was added to give a precipitate that was collected and washed with ether to give a purple solid (0.75 g, 7.1%): IR (neat) 2944, 1653, 1471, 1255, 1116, 1019 cm$^{-1}$; $^1$H NMR (CDCl$_3$, 300 MHz) δ8.15 (s, 1H), 7.69 (s, 1H), 7.02 (s, 1H), 4.11 (s, 3H), 4.05 (s, 3H), 4.02 (s, 3H) 3.99 (s, 6H), 3.91 (s, 3H); CIMS m/z (relative intensity) 412 ($MH^+$, 100).

Example 31 cis-4-Carboxy-3,4-dihydro-N-methyl-3-(3',4',5'-trimethoxyphenyl)-1(2H)isoquinolone (12j)

Homophthalic anhydride (10a) (0.32 g, 2 mmol) was added to a stirred solution of 3,4,5-trimethoxybenzylidenemethylamine (11i) (0.46 g, 2 mmol) in chloroform (5 mL). After 45 min, ether was added dropwise to the homogenous mixture and the resulting precipitate was filtered from the yellow solution and washed with ether to give a pale yellow solid (0.43 g, 60%): mp 194–195° C.; IR (neat) 2830, 1620, 1549, 1459, 1185, 1123 cm$^-$; $^1$H NMR (CDCl$_3$, 300 MHz) δ8.13 (s, 1H), 7.99 (d, 1H, J=7.2 Hz), 7.52 (m, 4H), 6.32 (s, 2H), 5.04 (d, 1H, J=5.9 Hz), 4.63 (d, 1H, J=6.0 Hz), 3.58 (s, 3H), 3.55 (s, 6H), 2.94 (s, 3H); CIMS m/z (relative intensity) 372 ($MH^+$, 100). Anal. Calcd for $C_{20}H_{21}NO_6$: C, H, N.

Example 32

5,6-Dihydro-5,11-diketo-6-methyl-8,9,10-trimethoxy-11H-indeno[1,2-c]isoquinoline (13j)

Thionyl chloride (10 mL) was added with stirring to 12j (200 mg, 0.5 mmol). After 4 h, the reaction mixture was diluted with benzene (50 mL) and evaporated to dryness. The dark orange solid was dissolved in chloroform and ether was added to give a dark orange solid (16 mg, 10%): mp 194–195° C.; IR (neat) 2938, 1665, 1463, 1400, 1292, 1125, 1007, 976 cm$^{-1}$; $^1$H NMR (CDCl$_3$, 300 MHz) δ8.67 (d, 1H, J=7.8 Hz), 8.32 (d, 1H, J=8. 0 Hz), 7.68 (t, 1H, J=8.0 Hz), 7.45 (t, 1H, J=7.8 Hz), 7.04 (s, 1H), 4.09 (s, 3H), 4.06 (s, 3H), 3.97 (s, 3H), 3.89 (s, 3H); CIMS m/z (relative intensity) 352 ($MH^+$, 100). Anal. Calcd for $C_{20}H_{17}NO_5$: C, H, N.

Example 33

3,4-Methylenedioxybenzylideneethylamine (11k)

Piperonal (20.1 g, 0.14 mol) and a 70% aqueous solution of ethylamine (20 mL) were stirred at room temperature for 3 h. The mixture was extracted with ether (4×50 mL). The ether layers were combined and washed with aqueous sodium chloride (50 mL), dried (MgSO$_4$) and concentrated under reduced pressure to give a white crystalline powder (24.56 g, 93%): mp 47–48° C.; IR (KBr) 2963, 2836, 1645, 1603, 1498, 1480, 1441, 1252, 1092, 1031, 959, 926 cm$^{-1}$; $^1$H NMR (CDCl$_3$, 300 MHz) δ8.15 (s, 1H), 7.32 (d, 1H, J=1.3 Hz), 7.09 (dd, 1H, J=1.4, 6.0 Hz), 6.80 (d, 1H, J=8.0), 5.98 (s, 2H) 3.59 (qd, 2H, J=6.0, 1.2 Hz), 1.26 (t, 3H, J=7.3 Hz); CIMS m/z (relative intensity) 178 (MH$^+$, 100). Anal. Calcd for C$_{10}$H$_{11}$NO$_2$: C, H, N.

Example 34 cis-4-Carboxy-N-ethyl-3-(3',4'-methylenedioxyphenyl)-6,7-dimethoxy3,4-dihydro-1(2H)isoquinolone (12k)

3,4-Methylenedioxybenzylideneethylamine (11k) (0.89 g, 5.0 mmol) was stirred in chloroform (5.0 mL) and 4,5-dimethoxyhomophthalic anhydride (10b) (1.11 g, 5.0 mmol) was added. After 30 min, the yellow precipitate was filtered and washed with chloroform to give a pale yellow solid (0.58 g, 29%): mp 231–233° C. (dec); IR (KBr) 2937, 1732, 1615, 1594, 1573, 1254, 1223, 1174, 1089, 1034, 986, 898 cm$^{-1}$; $^1$H NMR (DMSO, 300 MHz) δ7.50 (s, 1H), 7.15 (s, 1H), 6.76 (d, 1H, J=7.8 Hz), 6.57 (d, 1H, J=8.1 Hz), 6.48 (s, 1H), 5.94 (s, 2H), 5.03 (d, 1H, J=6.2 Hz), 4.51 (d, 1H, J=6.2 Hz), 3.79 (dq, 1H, J=6.9 Hz), 3.80 (s, 3H), 3.73 (s, 3H), 2.96 (dq, 1H, J=6.9 Hz), 1.01 (t, 3H, J=6.9 Hz); FABMS (m-NBA) m/z (relative intensity) 400 (MH$^+$, 100).

Example 35

6-Ethyl-5,6-dihydro-5,11-diketo-2,3-dimethoxy-8,9-methylenedioxy-11H-indeno[1,2-c]isoquinoline (13k)

Thionyl chloride (6.0 mL) was added with stirring to the cis acid 12k (0.58 g, 1.5 mmol) and the reaction mixture became dark reddish-purple and heterogeneous. After 4 h, the reaction mixture was diluted with benzene (5.0 mL) and evaporated to dryness. The brownish-red solid was loaded onto silica gel, passed through a short column of silica gel, eluting with chloroform, to give a brownish-red solid (0.34 g, 60%): mp 291–293° C.; IR 2969, 1694, 1643, 1613, 1555, 1486, 1393, 1308, 1252 cm$^{-1}$; $^1$H NMR (CDCl$_3$, 300 MHz) δ8.02 (s, 1H), 7.65 (s, 1H), 7.08 (s, 1H), 7.01 (s, 1H), 6.08 (s, 2H), 4.49 (q, 2H, J=7.2 Hz), 4.03 (s, 3H), 3.97 (s, 3H), 1.50 (t, 3H, J=7.2 Hz); CIMS m/z (relative intensity) 366 (MH$^+$, 4.0). Anal. Calcd for C$_{21}$H$_{17}$NO$_6$: C, H, N.

Example 36

General Procedure for the Synthesis of Imines 17

The O-TBDMS protected anisols 15 were synthesized using a reported procedure. The imines 17 were synthesized by treating the O-TBDMS protected aminols (9 mmol) with piperonal (9 mmol) in chloroform (20 mL) in the presence of anhydrous magnesium sulfate (2 g) at room temperature for 3 h. The imines were used as such for the next reaction without further purification. The crude yield of the imines 17 were quantitative.

Example 37

General Procedure for the Synthesis of Isoquinolones 18

4,5-Dimethoxyhomophthalic anhydride (10b) (2.22 g, 10 mmol) was added to a chloroform (20 mL) solution of the imine 17a of 17b (10 mmol) and the mixture was stirred at room temperature for 12 h, after which the TLC showed the complete disappearance of the starting materials and a white precipitate formed in the reaction mixture. The precipitated product was filtered off and washed with chloroform (5 mL) and dried to give pure 18a or 18b.

Example 38 cis-N-(t-Butyldimethylsilyloxybut-1-yl)-4-carboxy-3,4-dihydro-6,7dimethoxy-3-(3',4'-methylenedioxyphenyl)-1(2H)isoquinolone (18a)

The isoquinolone 18a was isolated in 36% yield: mp 239–240° C.; IR (KBr) 3065, 2944, 1737 cm$^{-1}$; $^1$H NMR (DMSO-d$_6$) δ7.51 (s, 1H), 7.11 (s, 1H), 6.75 (d, J=8.0 Hz, 1H), 6.54 (dd, J=1.3 and 8.1 Hz, 1H), 6.46 (d, J=1.2 Hz, 1H), 5.93 (s, 2H), 4.98 (d, J=6.1 Hz, 1H), 4.55 (d, J=6.1 Hz, 1H), 3.81 (s, 3H), 3.80–8.70 (m, 1H), 3.74 (s, 3H), 3.53 (t, J=5.78 Hz, 2H), 2.95–2.80 (m, 1H), 1.60–1.35 (m, 4H), 0.88 (s, 9H), –0.98 (s, 6H); $^{13}$C NMR (DMSO-d$_6$) δ170.64, 162.47, 151.21, 147.65, 147.00, 146.81, 131.26, 126.84, 121.55, 121.43, 110.85, 109.81, 107.87, 107.71, 101.06, 62.20, 61.01, 55.44, 47.77, 45.25, 29.67, 29.54, 25.81, 24.07, 17.91, –5.37; CIMS m/z (relative intensity) 558 (MH$^+$, 80). Anal. Calcd for C$_{29}$H$_{39}$NO$_8$Si: C, H, N.

Example 39 cis-N-(t-Butyldimethylsilyloxypent-1-yl)-4-carboxy-3,4-dihydro-6,7dimethoxy-3-(3',4'-methylenedioxyphenyl)-1(2H)isoquinolone (18b)

The isoquinolone 18b was isolated in 57% yield: mp 240–242° C.; IR (KBr) 3054, 2933, 1737 cm$^{-1}$; $^1$H NMR (DMSO-d$_6$) δ12.90 (bs, 1H), 7.51 (s, 1H), 7.09 (s, 1H), 6.75 (d, J=8.1 Hz, 1H), 6.55 (dd, J=1.6 and 8.1 Hz, 1H), 6.47 (d, J=1.3 Hz, 1H), 5.93 (s, 2H), 4.97 (d, J=6.2 Hz, 1H), 4.53 (d, J=6.2 Hz, 1H), 3.81 (s, 3H), 3.83–8.70 (m, 1H), 3.74 (s, 3H), 3.52 (t, J=6.2 Hz, 2H), 2.85–2.73 (m, 1H), 1.60–1.30 (m, 6H), 0.82 (s, 9H), –0.99 (s, 6H). CIMS m/z (relative intensity) 572 (MH$^-$, 100). Anal. Calcd for C$_{30}$H$_{41}$NO$_8$Si: C, H, N.

Example 40

General Procedure for the Synthesis of Indenoisoquinolines 19

Thionyl chloride (10 mL) was added dropwise to the acid 18 (2 mmol) with stirring. The resulting solution was stirred at room temperature for 5 h after which the solution turned purple. Benzene (20 mL) was added to the reaction mixture and it was concentrated under reduced pressure. The resulting residue was passed through a short column of silica gel (230–400 mesh) eluting with chloroform:methanol (95:5). Concentration of the eluent resulted in a pink solid which was crystallized from ethyl acetate to obtain pure indenoisoquinolines 19. Under the reaction conditions the deprotection of the O-TBDMS group was observed and only the hydroxy compounds were isolated.

Example 41

5,6-Dihydro-5,11-diketo-6-(4-hydroxybut-1-yl)-2,3-dimethoxy-8,9-methylenedioxy-(11H)indeno[1,2-c]isoquinoline (19a)

The indenoisoquinoline 19a was isolated in 84% yield: mp 304–308° C.; IR (KBr) 3432, 2929, 1696, 1645, 1610 cm$^{-1}$; $^1$H NMR (DMSO-d$_6$, 65° C.) δ7.91 (s, 1H), 7.53 (s, 1H), 7.53 (s, 1H), 7.06 (s, 1H), 6.17 (s, 1H), 4.43 (t, J=7.7 Hz, 2H), 3.90 (s, 3H), 3.86 (s, 3H), 3.45 (t, J=5.8 Hz, 2H), 1.88–1.70 (m, 2H), 1.60–1.50 (m, 2H); CIMS m/z (relative intensity) 424 (MH$^+$, 100). Anal. Calcd for C$_{23}$H$_{21}$NO$_7$ 0.5 H$_2$O: C, H, N.

Example 42

5,6-Dihydro-6-(4-hydroxypent-1-yl)-5,11-diketo-2, 3-dimethoxy-8,9-methylenedioxy-11H-indenoisoquinoline (19b)

The indenoisoquinoline 18b was isolated in 79% yield: mp 288–290° C.; IR (KBr) 3411, 2929, 1698, 1653, 1582, 1550 cm$^{-1}$; $^1$H NMR (DMSO-d$_6$, 80° C.) δ7.91 (s, 1H), 7.53 (s, 1H), 7.21 (s, 1H), 7.07 (s, 1H), 6.18 (s, 1H), 4.41 (bs, 2H), 3.90 (bs, 3H), 3.86 (s, 3H), 3.60 (bs, 1H), 3.40 (bs, 1H), 1.88–1.70 (m, 2H), 1.60–1.40 (m, 4H); CIMS m/z (relative intensity) 438 (MH$^+$, 100). Anal. Calcd for C$_{23}$H$_{21}$NO$_7$ 0.3 H$_2$O: C, H, N.

Example 43 cis-5,6,12,13-Tetrahydro-2,3-dimethoxy-6-methyl-5, 11-dioxo-8,9(methylenedioxy)-(11H)indeno[1,2-c]isoquinoline (20)

This compound was prepared as described previously in *J. Med. Chem.* 1984, 27, 544–547.

Example 44 cis-6-Ethyl-5,6,12,13-tetrahydro-2,3-dimethoxy-5, 11-dioxo-8,9-(methylene-dioxy)-11H-indeno[1,2-c]isoquinoline (21)

The acid 12k (3.99 g, 3 mmol) was added slowly under nitrogen to a solution of degassed Eaton's reagent (10% P$_2$O$_5$ in methanesulfonic acid, 120 mL) with stirring over a period of 20 min. The reaction mixture was stirred at room temperature for 4 h, after which the mixture was added dropwise to water (600 mL) with stirring. The precipitated white solid was filtered off and dissolved in chloroform (150 mL). The chloroform layer was washed with saturated NaHCO$_3$ solution (2×50 mL), water (50 mL), brine (60 mL) and dried (Na$_2$SO$_4$). Concentration of the organic layer gave the crude product, which was purified by column chromatography (4:1, hexane:ethyl acetate) to obtain pure 21 as a white solid (2.39 g, 63%). Neutralization of the bicarbonate layer with concd HCl gave the unreacted acid (0.821 g) as a white solid. Thus the yield based on the recovered starting acid is 79.3%. An analytical sample was prepared by recrystallization from EtOAc-Hexane (1:1) to yield white prisms: mp 169–170° C.; IR (KBr) 3006, 2994, 1706, 1642, 1601 cm$^{-1}$; $^1$H NMR (CDCl$_3$) δ7.59 (s, 1H), 7.16 (s, 1H), 7.06 (s, 1H), 7.00 (s, 1H), 6.09 (s, 1H), 6.04 (s, 1H), 5.04 (d, J=6.9 Hz, 1H), 4.70–4.53 (m, 1H), 4.21 (d, J=7.0 Hz, 1H), 3.94 (s, 3H), 3.88 (s, 3H), 3.40–3.26 (m, 1H), 1.35 (t, J=7.1 Hz, 3H); $^{13}$C NMR (CDCl$_3$) δ198-8 , 162.0, 154.7, 152.0, 150.6, 149.4, 148.5, 128.8, 126.4, 120.3, 110.2, 108.6, 104.2, 102.6, 56.6, 56.0, 55.8, 50.4, 43.3, 13.2. Anal. Calcd for C$_{21}$H$_{19}$NO$_6$: C, H, N.

Example 45 cis-6-Allyl-5,6,12,13-tetrahydro-2,3-dimethoxy-5, 11-dioxo-8,9-(methylenedioxy)-(11H)indeno[1,2-c]isoquinoline (22)

Indenoisoquinoline 22 was synthesized in 72% yield from the acid 12c in a similar procedure for the synthesis of indenoisoquinoline 21. The treatment of the isoquinolone 12c (4.11 g, 10 mmol) with Eaton's reagent (120 mL) provided the indenoisoquinoline 22 in 72% (2.83 g) yield: mp 178–180° C.; IR (KBr) 2990, 1708, 1642, 1600 cm$^{-1}$; $^1$H NMR (CDCl$_3$) δ7.60 (s, 1H), 7.17 (s, 1H), 7.07 (s, 1H), 7.03 (s, 1H), 6.09 (s, 1H), 6.05 (s, 1H), 6.05–5.90 (m, 1H), 5.45–5.20 (m, 3H), 5.16 (d, J=6.9 Hz, 1H), 4.19 (d, J=6.9 Hz, 1H), 3.94 (s, 3H), 3.88 (s, 3H), 3.90–3.80 (m, 1H); $^{13}$C NMR (CDCl$_3$) δ198.8, 162.3, 154.8, 152.3, 150.6, 149.5, 148.6, 132.6, 129.0, 126.6, 120.0, 118.0, 110.4, 108.7, 104.4, 102.7, 102.6, 56.3, 56.1, 55.9, 50.3. Anal. Calcd for C$_{22}$H$_{19}$NO$_6$: C, H, N.

Example 46

5,6-Dihydro-5,11-diketo-2,3,8-trimethoxy-6-methyl-9[(methylsulfonyl)oxy]-(11H)indeno[1,2-c]isoquinoline (23)

This compound was prepared as described previously in *J. Med. Chem.* 1985, 28, 1031–1036.

Example 47

6-Ethyl-5,6,12α,13α-tetrahydro-11β-hydroxy-2,3-dimethoxy-8,9-(methylenedioxy)-5-oxo-11H-indeno[1,2-c]isoquinoline (24)

The indenoisoquinoline 21 (0.381 g, 1 mmol) was heated at reflux with a 1 M solution of borane-tetrahydrofuran complex (4 mL) in dry THF (30 mL) for 1 h. After cooling, the reaction mixture was concentrated and the residue was dissolved in EtOAc (60 mL) and glacial acetic acid was added dropwise until pH 5. The organic layer was washed with saturated sodium bicarbonate (2×50 mL), brine, and dried (Na$_2$SO$_4$) and concentrated. The residue on chromatographic purification (2% methanol in chloroform as eluent) provided the pure product 24 (0.363 g, 95%). An analytical sample was prepared by recrystallization from EtOAc-hexane (3:1) to yield white prisms: mp 189–192° C.; IR (KBr) 3468, 2919, 1630, 1594 cm$^{-1}$; $^1$H NMR (CDCl$_3$) δ7.62 (s, 1H), 6.95 (s, 1H), 6.94 (s, 1H), 6.74 (s, 1H), 5.99 (s, 1H), 5.98 (s, 1H), 4.97 (dd, J=5.8 and 7.6 Hz, 1H), 4.89 (d, J=6.4 Hz, 1H), 3.94 (s, 3H), 3.93 (s, 3H), 3.90–3.73 (m, 1H), 3.59 (t, J=5.8 Hz, 1H), 3.45–3.30 (m, 1H), 2.03 (d, J=7.6 Hz, 1H, D$_2$O exchangeable), 1.03 (t, J=7.1 Hz, 3H); $^{13}$C NMR (CDCl$_3$) δ162.8, 152.1, 148.5, 148.4, 148.3, 138.7, 135.2, 128.2, 122.8, 110.5, 109.2, 106.6, 106.0, 101.5, 77.4, 60.0, 55.9, 55.8, 48.3, 37.9, 12.0. Anal. Calcd for C$_{21}$H$_{21}$NO$_6$: C, H, N.

Example 48

6-Ethyl-5,6,12α,13α-tetrahydro-11β-hydroxy-2,3-dimethoxy-8,9-(methylenedioxy)-11H-indeno[1,2-c]isoquinoline (25)

The indenoisoquinoline 21 (2.391 g, 6.27 mmol) was heated at reflux with a 1M solution of borane-tetrahydrofuran complex (15 mL) in dry THF (100 mL) for 12 h. After cooling, the reaction mixture was concentrated and the residue was dissolved in EtOAc (100 mL) and glacial acetic acid was added dropwise until pH 5. The organic layer was washed with saturated sodium bicarbonate (2×100 mL), brine, and dried (Na$_2$SO$_4$) and concentrated. The residue on chromatographic purification (5% ethyl acetate in chloroform as eluent) provided the pure product 25 (2.13 g, 92%). An analytical sample was prepared by recrystallization from isopropanol to yield white crystals:

mp 180–184° C.; IR (KBr) 3479, 2909, 1605, 1594 cm$^{-1}$; $^1$H NMR (CDCl$_3$) δ7.76 (s, 1H), 6.90 (s, 1H), 6.77 (s, 1H), 6.66 (s, 1H), 6.040 (s, 1H), 6.02 (s, 1H), 5.34 (dd, J=3.1 and 6.6 Hz, 1H), 4.90 (d, J=8.4 Hz, 1H), 4.15 (d, J=16.2 Hz, 1H), 4.06 (d, J=16.2 Hz, 1H), 3.93 (s, 3H), 3.89 (s, 3H) 371 (t, J=7.5 Hz, 1H), 2.86–2.70 (m, 1H), 2.20–2.13 (m, 1H), 2.03 (d, J=3.1 Hz, 1H, D$_2$O exchangeable 1.02 (t, J=7.1 Hz, 3H); $^{13}$C NMR (CDCl$_3$) δ149.4, 149.3, 148.4, 137.9, 131.2, 124.3, 123.4, 110.4, 110.1, 109.9, 104.7, 101.6, 74.0, 73.6, 58.0, 56.2, 56.0, 46.8, 45.6, 9.00. Anal. Calcd for C$_{21}$H$_{19}$NO$_6$·1.5 H$_2$O: C, H, N.

Example 49

6-(3-Carboxy-1-propyl)-5,6-dihydro-5,11-diketo-11H-indeno[1,2-c]isoquinoline (26)

The indenoisoquinoline 7 (0.319 g, 1 mmol) was dissolved in acetone (50 mL) and cooled in an ice bath. Jones reagent was added dropwise to the cold solution of the alcohol until the red color of the reagent persisted. The excess Jones reagent was quenched by adding few drops of isopropyl alcohol. The reaction mixture was filtered through a small pad of celite and the residue was washed with acetone (50 mL). The combined filtrate was concentrated and the residue was dissolved in saturated bicarbonate (100 mL) and the aqueous layer was washed with chloroform (2×30 mL). The aqueous layer was neutralized with concd HCl and extracted in CHCl$_3$ (3×50 mL). The combined organic layer was dried (Na$_2$SO$_4$) and concentrated to afford the acid as an orange solid. The solid was crystallized from isopropyl alcohol to yield orange crystals (0.320 g, 96%): mp 204–206° C.; IR (KBr) 3000 (b), 1708, 1698, 1654 cm$^{-1}$; $^1$H NMR (CDCl$_3$) δ8.68 (d, J=8 Hz, 1H), 8.30 (d, J=8 Hz, 1H), 7.86 (d, J=7.4Hz, 1H), 7.73 (t, J=8.0 Hz, 1H), 7.61 (d, J=7.2 Hz, 1H), 7.50–7.30 (m, 3H), 4.60 (t, J=7.8 Hz, 2H), 3.71 (s, 1H), 2.60 (t, J=7.0 Hz, 2H), 2.19 (p, J=7.0 Hz, 2H). Anal. Calcd for C$_2$ H$_{15}$NO$_4$: C, H, N.

Example 50

6-Ethyl-2,3-dimethoxy-8,9-(methylenedioxy)-11H-indeno[1,2-c]isoquinolinium Chloride (27)

The amino alcohol 25 (0.738 g, 2 mmol) was heated at reflux with 5% palladium on charcoal (0.265 g) in glacial acetic acid (100 mL) for 20 h. After cooling, the mixture was filtered through a small pad of celite, and the solvent was evaporated to give a brown residue. The residue was dissolved in water (50 mL) and ethanol (6 mL) to give a light brown solution, to which was added 15% aqueous sodium chloride (10 mL). A yellow product precipitated immediately and was filtered, washed with ice cold water (10 mL), and dried over P$_2$O$_5$ under vacuum overnight to yield a yellow powder (0.552 g, 72%). An analytical sample was crystallized from methanol: mp 340–343° C. (dec); IR (KBr) 3382, 1480, 1305 and 1210 cm$^{-1}$; H NMR (MeOH-d$_4$) δ9.27 (s, 1H), 7.61 (s, 2H), 7.46 (s, 1H), 7.30 (s, 1H), 6.15 (s, 2H), 5.03 (q, J=7.2 Hz, 2H), 4.87 (s, 2H), (s, 3H), 4.05 (s, 3H), 1.75 (t, J=7.2 Hz, 3H). $^{13}$C NMR (MeOH-d$_4$) δ189.5, 162.4, 155.7, 155.0, 152.5, 147.3, 133.4, 130.8, 127.9, 123.6, 107.5, 107.3, 106.6, 105.4, 101.5, 57.7, 57.1, 54.8, 15.7. Anal. Calcd for C$_{21}$H$_{20}$NO$_4$Cl·H$_2$O: C, H, N.

Example 51

Topoisomerase I-Mediated DNA Cleavage Reactions Using 3'-End-labeled 161 BP Plasmid DNA The 161 bp fragment from pBluescript SK(−) phagemid DNA (Stratagene, La Jolla, Calif.) was cleaved with the restriction endonuclease Pvu II and Hind III (New England Biolabs, Beverly, Mass.) in supplied NE buffer 2 (10 μL reactions) for 1 h at 37° C., separated by electrophoresis in a 1% agarose gel made in 1×TBE buffer. The 161 bp fragment was eluted from the gel slice (centrilutor by Amicon) and concentrated in a centricon 50 centrifugal concentrator (Amicon, Beverly, Mass.). Approximately 200 ng of the fragment was 3'-end-labeled at the Hind III site by fill-in reaction with [alpha-$^{32}$P]-dCTP and 0.5 mM dATP, dGTP, and dTTP, in React 2 buffer (50 mM Tris-HCl, pH 8.0, 100 mM MgCl, 50 mM NaCl) with 0.5 units of DNA polymerase I (Klenow fragment). Labeling reactions were followed by phenol-chloroform extraction and ethanol precipitation. The resulting 161 bp 3'-endlabeled DNA fragment was resuspended in water. Aliquots (approximately 50,000 dpm/reaction) were incubated with topoisomerase I at 30° C. for 15 min in the presence of the indicated drug. Reactions were terminated by adding 0.5% SDS. After ethanol precipitation, the samples were resuspended in loading buffer (80% formamide, 10 mM sodium hydroxide, 1 mM sodium EDTA, 0.1% xylene cyanol, and 0.1% bromophenol blue, pH 8.0), and separated in a denaturing gel (16% polyacrylamide, 7 M urea) run at 51° C. The gel was dried and visualized by using a Phosphoimager and ImageQuant software (Molecular Dynamics, Sunnyvale, Calif.).

Example 52

Topoisomerase II-Mediated DNA Cleavage Assays Using 5'-End-labeled Human C-myc DNA A 403-base pair DNA fragment of the human c-myc gene from the junction between the first intron and the first exon was prepared by PCR between positions 2671 and 3073 using the oligonucleotides 5'-TGCCGCATCCACGAAACTTTGC-3' as sense primer and 5'-GAACTGTTCAGTGTTTACCCCG-3' as antisense primer. Single-end labeling of these DNA fragments was obtained by 5'-end labeling of the adequate primer oligonucleotide. Approximately 0.1 μg of the human c-myc DNA that had been restricted by XhoI and XbaI was used as template for PCR. The 5'-end-labeled DNA fragments were equilibrated with or without a drug in 1% dimethyl sulfoxide, 10 mM Tris-HCl, pH 7.5, 50 mM KCl, 5 mM MgCl$_2$, 2 mM dithiothreitol, 0.1 mM Na$_2$EDTA, 1 mM ATP, and 15 μg/mL bovine serum albumine for 5 min before addition of purified human topoisomerase II (40–70 ng) in a 10 μL final reaction volume. The reactions were performed at 37° C. for 30 min and thereafter stopped by adding 1% sodium dodecyl sulfate (SDS) and 0.4 mg/ML proteinase K (final concentrations) followed by an additional incubation at 50° C. for 30 min. Samples were ethanol-precipitated before separation of the topoisomerase II-cleaved fragments on denaturing polyacrylamide gels. The sequencing gels were made of 7% polyacrylamide in 1×TBE buffer (90 mM Tris borate, 2 mM EDTA, pH 8.3). Electrophoresis was performed at 2500 V (60 W) for 2–5 h. The gels were dried and visualized using a Phosphoimager and ImageQuant software.

Example 53

SV40 DNA Unwinding Assay

Reaction mixtures (10 μL final volume) contained 0.3 μg supercoiled SV40 DNA in reaction buffer (10 mM Tris-HCl, pH 7.5, 50 mM KCl, 5 MM MgCl$_2$, 0.1 mM EDTA, 15 μ/mL bovine serum albumin) and 10 units of purified calf thymus topoisomerase I. Reactions were performed at 37° C. for 30 min and terminated by the addition of 0.5% SDS, and then 1.1 μL of 10×loading buffer (20% Ficol 400, 0.1 M Na$_2$EDTA pH 8, 1.0% SDS. 0.25% Bromophenol Blue) was then added and reaction mixtures were loaded onto a 1% agarose gel made in 1×TBE buffer. After electrophoresis, DNA bands were stained in 10 μg/mL of ethidium bromide and visualized by transillumination with UV light (300 nm).

What is claimed is:

1. A compound of the formula:

wherein
R$_1$ is hydrogen, formyl, phenyl, phenyl substituted with C$_1$–C$_6$ alkoxy, phenyl substituted with C$_1$–C$_6$ alkyl, or —(CH$_2$)$_m$Z, wherein m is 1–6 and Z is selected from the group consisting of hydrogen, hydroxy, carboxy, formyl, C$_1$–C$_6$ alkyl, carbo-(C$_1$–C$_6$ alkoxy), C$_2$–C$_6$ alkenyl, phenyl, C$_1$–C$_6$ alkylamino, and C$_1$–C$_6$ hydroxyalkylamino;

R$_2$, R$_2$' and R$_4$ are independently selected from the group consisting of hydrogen, C$_1$–C$_6$ alkyl, C$_2$–C$_6$ alkenyl, C$_1$–C$_6$ alkoxy, phenoxy, and benzyloxy, or R$_2$ and R$_2$', taken together, form —OCH$_2$O—;

R$_3$ and R$_3$' are independently selected from the group consisting of C$_1$–C$_6$ alkyl, C$_1$–C$_6$ alkoxy, C$_2$–C$_6$ alkenyl, phenoxy, and benzyloxy, or R$_3$ and R$_3$', taken together, form —OCH$_2$O—;

n=1 or 0, and bond a is a single bond when n=1, and bond a is a double bond when n=0;

provided that, when R$_2$ and R$_2$' are CH$_3$O, R$_3$ and R$_3$', taken together, form —OCH$_2$O—, R$_4$ is hydrogen, and n=0, R$_1$ is not —CH$_2$CH$_3$ or —CH$_2$Ph; and further provided that, when R$_1$ is methyl, R$_3$ and R$_3$' are independently selected from the group consisting of C$_1$–C$_6$ alkyl, C$_1$–C$_6$ alkoxy, C$_2$–C$_6$ alkenyl, phenoxy, and benzyloxy.

2. A compound of the formula:

wherein
R$_1$ is phenyl or phenyl substituted with C$_1$–C$_6$ alkoxy or C$_1$–C$_6$ alkyl, or R$_1$ is a group —(CH$_2$)$_m$Z wherein m is 1–6 and Z is selected from the group consisting of hydrogen, hydroxy, carboxy, formyl, C$_1$–C$_6$ alkyl, carbo-(C$_1$–C$_6$ alkoxy), C$_2$–C$_6$ alkenyl, phenyl, C$_1$–C$_6$ alkylamino, and C$_1$–C$_6$ hydroxyalkylamino;

R$_2$, R$_2$' and R$_4$ are independently selected from the group consisting of hydrogen, C$_1$–C$_6$ alkyl, C$_2$–C$_6$ alkenyl, C$_1$–C$_6$ alkoxy;

R$_3$ and R$_3$' are independently selected from the group consisting of hydrogen, C$_1$–C$_6$ alkyl, C$_1$–C$_6$ alkoxy, C$_2$–C$_6$ alkenyl, phenoxy, and benzyloxy, or R$_3$ and R$_3$' taken together form a group of the formula —OCH$_2$O—;

provided that, when Z is hydrogen, m is 2–6;

X is a pharmaceutically acceptable anion; and when R$_2$ and R$_2$' are hydrogen, R$_3$ and R$_3$', taken together, form —OCH$_2$O—, and Z is not C$_1$–C$_6$ alkyl.

3. A pharmaceutical composition for treatment of cancer comprising a compound of claim 1 in an amount effective for treatment of said cancer, and a pharmaceutically acceptable carrier, excipient, or diluent therefor.

4. A method for treating a patient having cancer, said method comprising the step of administering to the patient an effective amount of a compound according to claim 1, whereupon said patient is treated for cancer, and wherein the cancer is melanoma.

5. A pharmaceutical composition for treatment of cancer comprising a compound of claim 2 in an amount effective for treatment of said cancer, and a pharmaceutically acceptable carrier, excipient, or diluent therefor.

6. A method for treating a patient having cancer, said method comprising the step of administering to the patient an effective amount of a compound according to claim 2, whereupon said patient is treated for cancer, and wherein the cancer is melanoma.

7. The compound of claim 1 wherein:
R$_1$ is ethyl;
R$_2$ and R$_2$' are independently selected from hydrogen and methoxy;
R$_3$ and R$_3$', taken together, form —OCH$_2$O—; and
R$_4$ is hydrogen;
provided that, when R$_2$ and R$_2$' are CH$_3$O, R$_3$ and R$_3$', taken together, form —OCH$_2$O—, R$_4$ is hydrogen, and n is not equal to 0.

8. A pharmaceutical composition for treatment of cancer comprising a compound of claim 7 in an amount effective for treatment of said cancer, and a pharmaceutically acceptable carrier, excipient, or diluent therefor.

9. A method for treating a patient having cancer, said method comprising the step of administering to the patient an effective amount of a compound according to claim 7, whereupon said patient is treated for cancer, and wherein the cancer is melanoma.

10. A compound of the formula:

wherein
R$_1$ is hydrogen, formyl, phenyl substituted with C$_1$–C$_6$ alkoxy, phenyl substituted with C$_1$–C$_6$ alkyl, or —(CH$_2$)$_m$Z, wherein m is 1–6 and Z is selected from the group consisting of hydrogen, hydroxy, carboxy, formyl, carbo-($C_1$–$C_6$ alkoxy), $C_2$–$C_6$ alkenyl, phenyl, $C_1$–$C_6$ alkylamino, and $C_1$–$C_6$ hydroxyalkylamino;

$R_2$, $R_2'$ and $R_4$ are independently selected from the group consisting of hydrogen, $C_1$–$C_6$ alkyl, $C_2$–$C_6$ alkenyl, $C_1$–$C_6$ alkoxy, phenoxy, and benzyloxy, or $R_2$ and $R_2'$, taken together, form —OCH$_2$O—;

$R_3$ and $R_3'$ are independently selected from the group consisting of hydrogen, $C_1$–$C_6$ alkyl, $C_1$–$C_6$ alkoxy, $C_2$–$C_6$ alkenyl, phenoxy, and benzyloxy, or $R_3$ and $R_3'$, taken together, form —OCH$_2$O—;

n=1 or 0, and bond a is a single bond when n=1, and bond a is a double bond when n=0;

provided that, when $R_2$, $R_2'$, $R_4$, $R_3$ and $R_3'$ are hydrogen and n=0, Z is not $C_1$–$C_6$ hydroxyalkylamino and $R_1$ is not hydrogen, —CH$_2$CH=CH$_2$, or —(CH$_2$)$_2$OH;

further provided that, when any four substituents of $R_2$, $R_2'$, $R_4$, $R_3$ and $R_3'$ are hydrogen and n=0, Z is not $C_1$–$C_6$ hydroxyalkylamino; and further provided that, when $R_2$ and $R_2'$ are CH$_3$O, $R_3$ and $R_3'$, taken together, form —OCH$_2$O, $R_4$ is hydrogen, and n=0, $R_1$ is not —CH$_2$Ph.

11. A pharmaceutical composition for treatment of cancer comprising a compound of claim 10 in an amount effective for treatment of said cancer, and a pharmaceutically acceptable carrier, excipient, or diluent therefor.

12. A method for treating a patient having cancer, said method comprising the step of administering to the patient an effective amount of a compound according to claim 10, whereupon said patient is treated for cancer, and wherein the cancer is melanoma.

13. The compound of claim 10 wherein:

$R_1$ is allyl, —(CH$_2$)$_3$COOH or —(CH$_2$)$_m$OH, wherein m is 4 or 5;

$R_2$ and $R_2'$ are independently selected from hydrogen and methoxy;

$R_3$ and $R_3'$ are hydrogen or, taken together, form —OCH$_2$O—; and $R_4$ is hydrogen;

provided that, when $R_2$, $R_2'$, $R_4$, $R_3$ and $R_3'$ are hydrogen and n=0, $R_1$ is not —CH$_2$CH=CH$_2$.

14. A pharmaceutical composition for treatment of cancer comprising a compound of claim 13 in an amount effective for treatment of said cancer, and a pharmaceutically acceptable carrier, excipient, or diluent therefor.

15. A method for treating a patient having cancer, said method comprising the step of administering to the patient an effective amount of a compound according to claim 13, whereupon said patient is treated for cancer, and wherein the cancer is melanoma.

16. A compound of the formula:

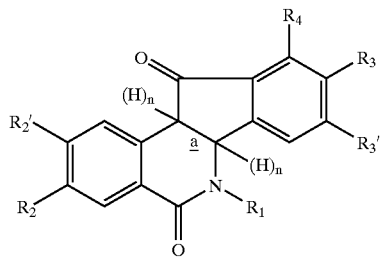

wherein $R_1$ is hydrogen, formyl, phenyl, phenyl substituted with $C_1$–$C_6$ alkoxy, phenyl substituted with $C_1$–$C_6$ alkyl, or —(CH$_2$)$_m$Z, wherein m is 1–6 and Z is selected from the group consisting of hydrogen, hydroxy, carboxy, formyl, $C_1$–$C_6$ alkyl, carbo-($C_1$–$C_6$ alkoxy), $C_2$–$C_6$ alkenyl, phenyl, $C_1$–$C_6$ alkylamino, and $C_1$–$C_6$ hydroxyalkylamino;

$R_2$, $R_2'$ and $R_4$ are independently selected from the group consisting of $C_1$–$C_6$ alkyl, $C_2$–$C_6$ alkenyl, $C_1$–$C_6$ alkoxy, phenoxy, and benzyloxy, or $R_2$ and $R_2'$, taken together, form —OCH$_2$O—;

$R_3$ and $R_3'$ are independently selected from the group consisting of hydrogen, $C_1$–$C_6$ alkyl, $C_1$–$C_6$ alkoxy, $C_2$–$C_6$ alkenyl, phenoxy, and benzyloxy, or $R_3$ and $R_3'$, taken together, form —OCH$_2$O—;

n=1 or 0, and bond a is a single bond when n=1, and bond a is a double bond when n=0; and provided that, when $R_1$ is methyl, $R_3$ and $R_3'$ are independently selected from the group consisting of hydrogen, $C_1$–$C_6$ alkyl, $C_1$–$C_6$ alkoxy, $C_2$–$C_6$ alkenyl, phenoxy, and benzyloxy.

17. A pharmaceutical composition for treatment of cancer comprising a compound of claim 16 in an amount effective for treatment of said cancer, and a pharmaceutically acceptable carrier, excipient, or diluent therefor.

18. A method for treating a patient having cancer, said method comprising the step of administering to the patient an effective amount of a compound according to claim 16, whereupon said patient is treated for cancer, and wherein the cancer is melanoma.

19. A method for treating a patient having cancer, said method comprising the step of administering to the patient an effective amount of a compound according to claim 1, whereupon said patient is treated for cancer, wherein the cancer is renal cancer.

20. A method for treating a patient having cancer, said method comprising the step of administering to the patient an effective amount of a compound according to claim 1, whereupon said patient is treated for cancer, wherein the cancer is lung cancer.

21. A method for treating a patient having cancer, said method comprising the step of administering to the patient an effective amount of a compound according to claim 1, whereupon said patient is treated for cancer, wherein the cancer is colon cancer.

22. A method for treating a patient having cancer, said method comprising the step of administering to the patient an effective amount of a compound according to claim 1, whereupon said patient is treated for cancer, wherein the cancer is ovarian cancer.

23. A method for treating a patient having cancer, said method comprising the step of administering to the patient an effective amount of a compound according to claim 1, whereupon said patient is treated for cancer, wherein the cancer is breast cancer.

24. A method for treating a patient having cancer, said method comprising the step of administering to the patient an effective amount of a compound according to claim 1, whereupon said patient is treated for cancer, wherein the cancer is prostate cancer.

25. A method for treating a patient having cancer, said method comprising the step of administering to the patient an effective amount of a compound according to claim 2, whereupon said patient is treated for cancer, wherein the cancer is renal cancer.

26. A method for treating a patient having cancer, said method comprising the step of administering to the patient an effective amount of a compound according to claim 2, whereupon said patient is treated for cancer, wherein the cancer is lung cancer.

27. A method for treating a patient having cancer, said method comprising the step of administering to the patient an effective amount of a compound according to claim 2, whereupon said patient is treated for cancer, wherein the cancer is colon cancer.

28. A method for treating a patient having cancer, said method comprising the step of administering to the patient an effective amount of a compound according to claim 2, whereupon said patient is treated for cancer, wherein the cancer is ovarian cancer.

29. A method for treating a patient having cancer, said method comprising the step of administering to the patient an effective amount of a compound according to claim 2, whereupon said patient is treated for cancer, wherein the cancer is breast cancer.

30. A method for treating a patient having cancer, said method comprising the step of administering to the patient an effective amount of a compound according to claim 2, whereupon said patient is treated for cancer, wherein the cancer is prostate cancer.

31. A method for treating a patient having cancer, said method comprising the step of administering to the patient an effective amount of a compound according to claim 7, whereupon said patient is treated for cancer, wherein the cancer is renal cancer.

32. A method for treating a patient having cancer, said method comprising the step of administering to the patient an effective amount of a compound according to claim 7, whereupon said patient is treated for cancer, wherein the cancer is lung cancer.

33. A method for treating a patient having cancer, said method comprising the step of administering to the patient an effective amount of a compound according to claim 7, whereupon said patient is treated for cancer, wherein the cancer is colon cancer.

34. A method for treating a patient having cancer, said method comprising the step of administering to the patient an effective amount of a compound according to claim 7, whereupon said patient is treated for cancer, wherein the cancer is ovarian cancer.

35. A method for treating a patient having cancer, said method comprising the step of administering to the patient an effective amount of a compound according to claim 7, whereupon said patient is treated for cancer, wherein the cancer is breast cancer.

36. A method for treating a patient having cancer, said method comprising the step of administering to the patient an effective amount of a compound according to claim 7, whereupon said patient is treated for cancer, wherein the cancer is prostate cancer.

37. A method for treating a patient having cancer, said method comprising the step of administering to the patient an effective amount of a compound according to claim 10, whereupon said patient is treated for cancer, wherein the cancer is renal cancer.

38. A method for treating a patient having cancer, said method comprising the step of administering to the patient an effective amount of a compound according to claim 10, whereupon said patient is treated for cancer, wherein the cancer is lung cancer.

39. A method for treating a patient having cancer, said method comprising the step of administering to the patient an effective amount of a compound according to claim 10, whereupon said patient is treated for cancer, wherein the cancer is colon cancer.

40. A method for treating a patient having cancer, said method comprising the step of administering to the patient an effective amount of a compound according to claim 10, whereupon said patient is treated for cancer, wherein the cancer is ovarian cancer.

41. A method for treating a patient having cancer, said method comprising the step of administering to the patient an effective amount of a compound according to claim 10, whereupon said patient is treated for cancer, wherein, the cancer is breast cancer.

42. A method for treating a patient having cancer, said method comprising the step of administering to the patient an effective amount of a compound according to claim 10, whereupon said patient is treated for cancer, wherein the cancer is prostate cancer.

43. A method for treating a patient having cancer, said method comprising the step of administering to the patient an effective amount of a compound according to claim 13, whereupon said patient is treated for cancer, wherein the cancer is renal cancer.

44. A method for treating a patient having cancer, said method comprising the step of administering to the patient an effective amount of a compound according to claim 13, whereupon said patient is treated for cancer, wherein the cancer is lung cancer.

45. A method for treating a patient having cancer, said method comprising the step of administering to the patient an effective amount of a compound according to claim 13, whereupon said patient is treated for cancer, wherein the cancer is colon cancer.

46. A method for treating a patient having cancer, said method comprising the step of administering to the patient an effective amount of a compound according to claim 13, whereupon said patient is treated for cancer, wherein the cancer is ovarian cancer.

47. A method for treating a patient having cancer, said method comprising the step of administering to the patient an effective amount of a compound according to claim 13, whereupon said patient is treated for cancer, wherein the cancer is breast cancer.

48. A method for treating a patient having cancer, said method comprising the step of administering to the patient an effective amount of a compound according to claim 13, whereupon said patient is treated for cancer, wherein the cancer is prostate cancer.

49. A method for treating a patient having cancer, said method comprising the step of administering to the patient an effective amount of a compound according to claim 16, whereupon said patient is treated for cancer, wherein the cancer is renal cancer.

50. A method for treating a patient having cancer, said method comprising the step of administering to the patient an effective amount of a compound according to claim 16, whereupon said patient is treated for cancer, wherein the cancer is lung cancer.

51. A method for treating a patient having cancer, said method comprising the step of administering to the patient an effective amount of a compound according to claim 16, whereupon said patient is treated for cancer, wherein the cancer is colon cancer.

52. A method for treating a patient having cancer, said method comprising the step of administering to the patient an effective amount of a compound according to claim 16, whereupon said patient is treated for cancer, wherein the cancer is ovarian cancer.

53. A method for treating a patient having cancer, said method comprising the step of administering to the patient an effective amount of a compound according to claim 16, whereupon said patient is treated for cancer, wherein the cancer is breast cancer.

54. A. method for treating a patient having cancer, said method comprising the step of administering to the patient an effective amount of a compound according to claim 16, whereupon said patient is treated for cancer, wherein the cancer is prostate cancer.

* * * * *

UNITED STATES PATENT AND TRADEMARK OFFICE
CERTIFICATE OF CORRECTION

PATENT NO. : 6,509,344 B1
DATED : January 21, 2003
INVENTOR(S) : Cushman et al.

It is certified that error appears in the above-identified patent and that said Letters Patent is hereby corrected as shown below:

Title page,
Item [73], Assignees, "The United States of America as represented by the Department of Health and Human Services, Washington, DC (US); Office of Technology Transfer National Institute of Health, Rockville, MD (US)" should read -- The United States of America as represented by the Department of Health and Human Services, Washington, DC (US); and Purdue Research Foundation, West Lafayette, IN (US) --.

Signed and Sealed this

Eleventh Day of January, 2005

JON W. DUDAS
*Director of the United States Patent and Trademark Office*